US012606787B2

(12) United States Patent
Igarashi

(10) Patent No.: US 12,606,787 B2
(45) Date of Patent: Apr. 21, 2026

(54) BIOLOGICAL COMPONENT CASSETTE, BIOLOGICAL COMPONENT KIT, AND BIOLOGICAL COMPONENT TREATMENT SYSTEM

(71) Applicant: TERUMO KABUSHIKI KAISHA, Tokyo (JP)

(72) Inventor: Masatsugu Igarashi, Shizuoka (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 944 days.

(21) Appl. No.: 17/697,546

(22) Filed: Mar. 17, 2022

(65) Prior Publication Data

US 2022/0204907 A1 Jun. 30, 2022

Related U.S. Application Data

(63) Continuation of application No. PCT/JP2020/034241, filed on Sep. 10, 2020.

(30) Foreign Application Priority Data

Sep. 20, 2019 (JP) ................................. 2019-171046

(51) Int. Cl.
*C12M 1/00* (2006.01)
*C12M 1/26* (2006.01)
*C12M 3/00* (2006.01)

(52) U.S. Cl.
CPC ............ *C12M 23/58* (2013.01); *C12M 23/14* (2013.01); *C12M 23/26* (2013.01); *C12M 23/42* (2013.01); *C12M 33/07* (2013.01)

(58) Field of Classification Search
CPC ...... C12M 23/58; C12M 23/14; C12M 23/26; C12M 23/42; C12M 33/07
See application file for complete search history.

(56) References Cited

U.S. PATENT DOCUMENTS 4,838,865 A 6/1989 Flank et al.
6,293,926 B1 * 9/2001 Sorensen ............ A61M 3/0201
417/477.2

(Continued)

FOREIGN PATENT DOCUMENTS

DE 102017106402 9/2018
JP 2008-543349 12/2008

(Continued)

OTHER PUBLICATIONS

U.S. Appl. No. 17/697,546, filed Mar. 17, 2022, Igarashi.

(Continued)

*Primary Examiner* — William H. Beisner
*Assistant Examiner* — Danielle B Henkel
(74) *Attorney, Agent, or Firm* — Sheridan Ross P.C.

(57) ABSTRACT

A biological component treatment system includes a biological component kit, and a biological component treatment device in which the biological component kit is set. The biological component kit includes tubes and a biological component cassette. The biological component cassette includes a cassette main body having flow paths in the interior of the cassette main body, and the cassette main body includes flow path opening/closing units which are capable of switching between opening and closing of the flow paths. The flow path opening/closing units include cutouts provided at positions adjacent to the flow paths.

20 Claims, 16 Drawing Sheets

(56) References Cited

U.S. PATENT DOCUMENTS

| | | | |
|---|---|---|---|
| 2003/0138334 A1 | 7/2003 | Vandlik et al. | |
| 2003/0199803 A1* | 10/2003 | Robinson | B04B 5/0442 |
| | | | 604/6.04 |
| 2004/0200909 A1 | 10/2004 | McMillian et al. | |
| 2005/0118048 A1* | 6/2005 | Traxinger | A61M 1/72 |
| | | | 417/477.2 |
| 2009/0163857 A1 | 6/2009 | Haddad et al. | |
| 2013/0304027 A1* | 11/2013 | Haddad | A61M 5/1685 |
| | | | 604/122 |
| 2014/0356941 A1 | 12/2014 | Bransky et al. | |
| 2017/0165436 A1* | 6/2017 | Haddad | A61M 5/16831 |
| 2019/0064168 A1 | 2/2019 | Handique et al. | |
| 2019/0231949 A1 | 8/2019 | Igarashi | |
| 2020/0093974 A1 | 3/2020 | Heide et al. | |
| 2020/0345906 A1 | 11/2020 | Igarashi | |

FOREIGN PATENT DOCUMENTS

| | | |
|---|---|---|
| JP | 2017-518365 | 7/2017 |
| JP | 2019-171037 | 10/2019 |
| JP | 2019-171046 | 10/2019 |
| WO | WO 2018/051982 | 3/2018 |
| WO | WO 2019/035415 | 2/2019 |

OTHER PUBLICATIONS

International Search Report and Written Opinion for International (PCT) Patent Application No. PCT/JP2020/034240, dated Dec. 4, 2020, 11 pages.

International Search Report and Written Opinion for International (PCT) Patent Application No. PCT/JP2020/034241, dated Dec. 21, 2020, 11 pages.

Official Action (English Translation) for Japan Patent Application No. 2022-509028, dated Aug. 6, 2024, 4 pages.

Official Action (with English translation) for Japan Patent Application No. 2022-509029, dated Apr. 16, 2024, 7 pages.

Official Action for U.S. Appl. No. 17/697,494, dated Jun. 12, 2025 15 pages.

Official Action for U.S. Appl. No. 17/697,494, dated Dec. 3, 2025 14 pages.

* cited by examiner

PUMP DRIVEN: ○  DRIVING OF PUMP STOPPED: ●
CLAMP OPENED: □  CLAMP CLOSED: ■

BIOLOGICAL COMPONENT CASSETTE, BIOLOGICAL COMPONENT KIT, AND BIOLOGICAL COMPONENT TREATMENT SYSTEM

CROSS REFERENCE TO RELATED APPLICATIONS

The present disclosure is a continuation of and claims benefit to PCT Application No. PCT/JP2020/034241 filed on Sep. 10, 2020, entitled "BIOLOGICAL COMPONENT CASSETTE, BIOLOGICAL COMPONENT KIT, AND BIOLOGICAL COMPONENT TREATMENT SYSTEM" which claims priority to Japanese Patent Application No. 2019-171046 filed on Sep. 20, 2019. The entire disclosures of the applications listed above are hereby incorporated by reference, in their entirety, for all that they teach and for all purposes.

BACKGROUND

The present disclosure relates to a biological component cassette having flow paths through which a biological component flows, a biological component kit including the biological component cassette, and a biological component treatment system constituted by the biological component kit and a biological component treatment device.

In the practice of regenerative medicine, biological cells (e.g., biological components) are collected and cultured, and the cultured cells are administered to a patient. In a process of culturing cells, for example, as disclosed in Japanese Laid-Open Patent Publication No. 2017-143775, a cell culturing device (e.g., a biological component treatment device), which is equipped with a cell culturing container (e.g., a bioreactor) having hollow fibers inside a case, is used. In this type of biological component treatment device, a biological component kit having a plurality of medical bags and a bioreactor is set, and after a liquid containing cells is supplied into the hollow fibers and the cells are made to adhere to inner circumferential surfaces of the hollow fibers, the cells are made to undergo propagation by supplying a culture medium into the cell culturing container.

SUMMARY

In the above type of biological component kit, a plurality of complicated pathways are formed between the plurality of medical bags and the bioreactor. Therefore, a problem arises in that time is required for an operator to set the biological component kit in the biological component treatment device, and further, mistakes are likely to occur when the biological component kit is mounted.

In some examples, constitution may be considered in which a plurality of pathways are integrated in a rigid biological component cassette, and the biological component cassette is set in the device. However, when such a rigid biological component cassette is applied, it becomes difficult to detect the state of the liquid flowing through the flow paths in the interior of the cassette, or to open and close the flow paths inside the biological component cassette, and constituent components of the flow paths must be provided on the exterior of the biological component cassette. In this case, in addition to setting the biological component cassette, an operation for setting the constituent components on the exterior of the cassette must take place, and working efficiency is not sufficiently improved.

The present disclosure has been devised in relation to the aforementioned technique, and has the object of, for example, providing a biological component cassette, a biological component kit, and a biological component treatment system, which enable ease of usage to be further enhanced, by making it possible to easily and accurately arrange a plurality of pathways therein, and to easily open and close the flow paths.

In order to achieve the aforementioned object, a first aspect of the present disclosure includes a biological component cassette having a flow path in interior thereof through which a liquid containing at least one biological component is allowed to flow, and including a cassette main body formed in a sheet shape that possesses flexibility, wherein the cassette main body includes a flow path opening/closing unit configured to switch between opening and closing of the flow path, and the flow path opening/closing unit includes a cutout provided at a position adjacent to the flow path, and which is cut out of the cassette main body in a thickness direction.

Further, in order to achieve the aforementioned object, a second aspect of the present disclosure includes a biological component cassette having a flow path in interior thereof through which a liquid containing at least one biological component is allowed to flow, and including a cassette main body formed in a sheet shape that possesses flexibility, wherein the cassette main body is constituted by joining together a pair of resin sheets, and so as to include the flow path between the resin sheets, and at least a portion of the flow path in the cassette main body includes a sheet separating portion in which an outer circumferential surface of the flow path is separated from the resin sheets over an entire circumference thereof.

Further, in order to achieve the aforementioned object, a third aspect of the present disclosure includes a biological component kit, including a tube through which a liquid containing at least one biological component is allowed to flow, and a biological component cassette to which the tube is connected, wherein the biological component cassette has a flow path in interior thereof through which the liquid is allowed to flow, and including a cassette main body formed in a sheet shape that possesses flexibility, the cassette main body includes a flow path opening/closing unit configured to switch between opening and closing of the flow path, and the flow path opening/closing unit includes a cutout provided at a position adjacent to the flow path, and which is cut out of the cassette main body in a thickness direction.

Further, in order to achieve the aforementioned object, a fourth aspect of the present disclosure includes a biological component treatment system, including a biological component kit including a tube through which a liquid containing at least one biological component is allowed to flow, and a biological component cassette to which the tube is connected, and a biological component treatment device in which the biological component kit is set, wherein the biological component cassette has a flow path in interior thereof through which the liquid is allowed to flow, and includes a cassette main body formed in a sheet shape that possesses flexibility, the cassette main body includes a flow path opening/closing unit configured to switch between opening and closing of the flow path, the flow path opening/closing unit includes a cutout provided at a position adjacent to the flow path, and which is cut out of the cassette main body in a thickness direction, and the biological component treatment device includes a displaceable body inserted into the cutout in a set state of the biological component kit, and which is configured to open and close the flow path in accordance with a displacement operation.

In the above-described biological component cassette, the biological component kit, and the biological component treatment system, a plurality of pathways can be easily and accurately arranged, and by easily opening and closing the flow paths, ease of usage can be further enhanced.

DETAILED DESCRIPTION

Embodiments of the present disclosure will be presented and described in detail below with reference to the accompanying drawings.

Figure 1:
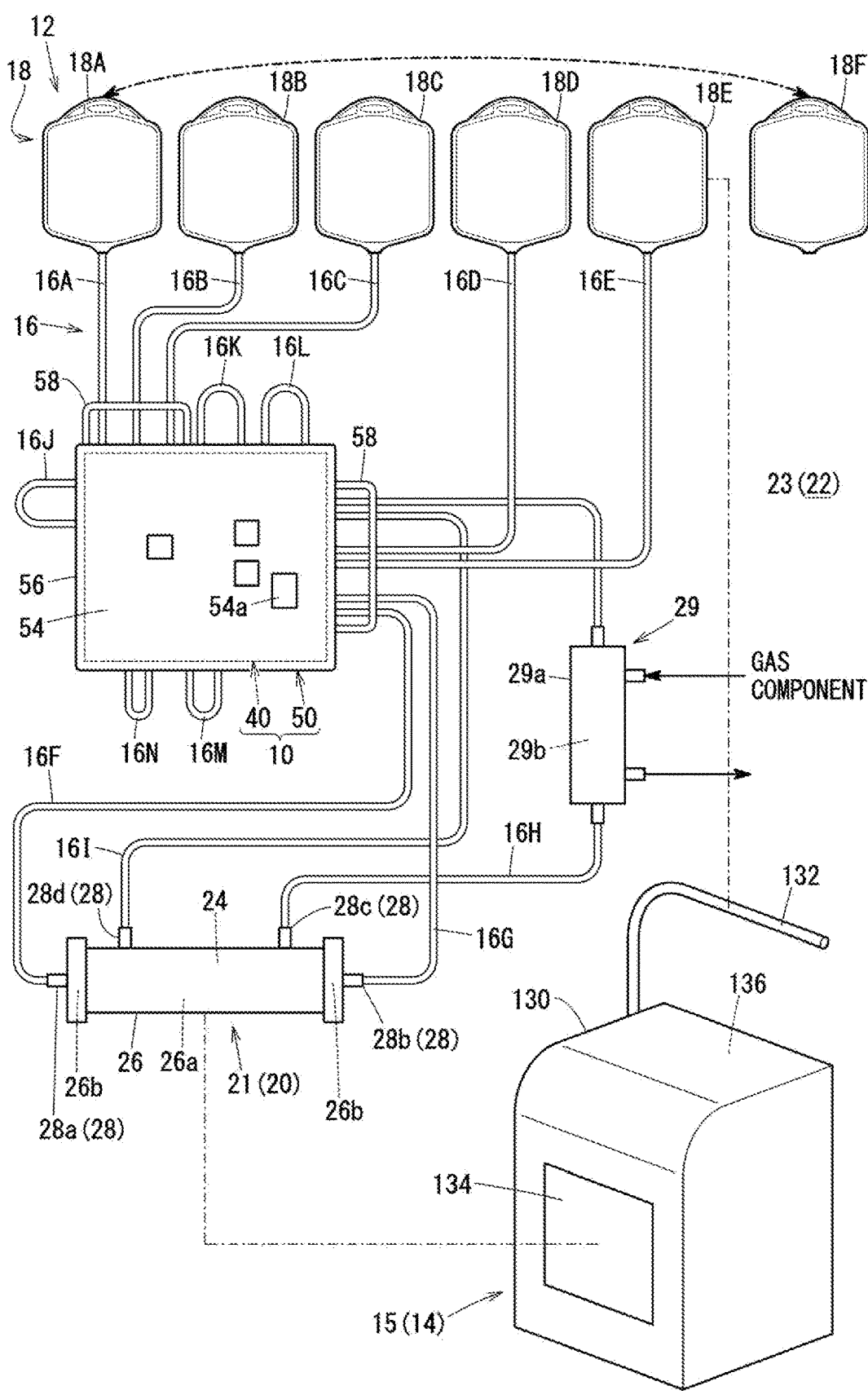
FIG. 1 is a schematic diagram showing a biological component treatment system to which a biological component cassette and a biological component kit are applied according to embodiments of the present disclosure.

A biological component cassette 10 (hereinafter, simply referred to as a cassette 10) according to at least one embodiment of the present disclosure, as shown in FIG. 1, comprises one part of a biological component kit 12 (hereinafter, simply referred to as a kit 12), and is set or disposed in a biological component treatment device 14. The cassette 10 collects together a plurality of pathways of the kit 12, and is used as a structural body through which a liquid containing a biological component and a liquid for processing of the biological component are capable of flowing or being circulated.

The kit 12 forms the plurality of pathways that pass through the cassette 10, and the kit 12 includes a plurality of tubes 16, a plurality of medical bags 18, and a treatment unit 20 in which processing is performed in the biological component treatment device 14. The kit 12 allows a plurality of types of liquids contained in each of the medical bags 18 to flow through the cassette 10 and through each of the tubes 16 under the operation of the biological component treatment device 14, and is constituted so as to obtain a target product by processing the liquids in the treatment unit 20.

The kit 12 according to at least one embodiment of the present disclosure is a cell propagation kit which is used in a propagation process for propagating biological cells (e.g., biological components) in regenerative medicine, and a bioreactor 21 that seeds and propagates the cells is applied to the treatment unit 20. Further, the liquids that flow inside the kit 12 may be or comprise a solution containing cells (hereinafter referred to as a cell solution), a culture medium (culture solution) which is supplied in order to propagate the cells, a cleaning solution for cleaning the interior of the kit 12, and/or a stripping solution for stripping the cells. More specifically, the kit 12 and the biological component treatment device 14 constitute a biological component treatment system 22 that seeds the bioreactor 21 with the cell solution, together with supplying the culture medium and thereby culturing the cells, and thereafter, strips and collects the propagated cells from the bioreactor 21. Hereinafter, the biological component treatment device 14 may also be referred to as a cell propagation device 15, and the biological component treatment system 22 may also be referred to as a cell propagation system 23.

The biological cells (e.g., cells of a living body) are not particularly limited, and may include, for example, cells (e.g., T cells and the like) contained in blood, and stem cells (e.g., ES cells, iPS cells, mesenchymal stem cells, and the like). An appropriate culture medium may be selected according to the biological cells and may contain, for example, a balanced salt solution (BSS) as a basic solution, various amino acids, vitamins, serum and/or the like in order to prepare the culture medium. Further, the cleaning solution is not particularly limited, and as examples thereof, there may be or comprise buffering solutions such as Phosphate Buffered Salts (PBS), Tris-Buffered Saline (TBS) and the like, or physiological saline. Further, the stripping solution may be or comprise, for example, trypsin or an EDTA solution.

The plurality of medical bags 18 of the kit 12 may include a cell solution bag 18A in which the cell solution is stored, a cleaning solution bag 18B in which the cleaning solution is stored, and/or a culture medium bag 18C in which the culture medium is stored. Furthermore, as the plurality of medical bags 18 of the kit 12 may include empty bags, and such empty bags may include a waste liquid bag 18D into which a liquid that is discarded in the propagation process flows, and a collection bag 18E in which cells (and other liquids) obtained in the propagation process are collected. Further, among the medical bags 18, a stripping solution bag 18F in which the stripping solution is stored is separately prepared. During the course of the propagation process, the stripping solution bag 18F is exchanged by an operator with one of the medical bags 18 (e.g., the cell solution bag 18A) that has been connected beforehand.

The cell solution bag 18A, the cleaning solution bag 18B, and the culture medium bag 18C, etc., are aseptically joined to ends of the respective tubes 16 using a non-illustrated aseptic joining device. Alternatively, each of the medical bags 18 may be fixed to ends of the respective tubes 16 in a non-separable manner, and may have a structure for ensuring sterility inside the kit 12. Further, alternatively, the kit 12 may apply a connection structure (not shown) that enables a detachable connection between the tubes 16 and each of the medical bags 18.

Although not particularly limited, for the bioreactor 21 of the kit 12, it may be preferable to use a culture medium base material having a large surface area, and for example, a structure having hollow fibers 24 may be applied thereto. More specifically, the bioreactor 21 may include a plurality of the hollow fibers 24 (e.g., ten thousand or more hollow fibers), and a cylindrical container 26 having a main space 26a therein in which the plurality of hollow fibers 24 are disposed.

The plurality of hollow fibers 24 include internal cavities (not shown) that penetrate along the direction of extension thereof, and the cells are cultured by becoming adhered on inner peripheral surfaces of the hollow fibers 24 that form the internal cavities. The respective hollow fibers 24 are arranged along an axial direction of the container 26, and both ends thereof are retained by non-illustrated retaining walls. The diameters of the hollow cavities, for example, are formed on the order of approximately 200 micrometers, and communicate with end spaces 26b on both axial sides of the retaining walls.

Further, the respective hollow fibers 24 include a plurality of non-illustrated pores therein that enable communication between the outer side (e.g., the main space 26a) and the internal cavities of the hollow fibers 24. The respective pores are formed with sizes that do not allow cells and proteins to pass, but on the other hand enable solutions and substances of low molecular weight to pass therethrough. The diameter of the pores is set, for example, on the order of 0.005 micrometers to 10 micrometers. Consequently, the culture medium, and a predetermined gas component and the like are supplied via the pores to the cells that are adhered to the inner peripheral surfaces of the hollow fibers 24. Hereinafter, circulation of liquid primarily in the internal cavities of the hollow fibers 24 may also be referred to as an intracapillary (IC) configuration, and circulation of liquid primarily on outer sides of the hollow fibers 24 may also be referred to as an extracapillary (EC) configuration.

The material of the hollow fibers 24 is not particularly limited, and may be or comprise, for example, polyolefin resins such as polypropylene, polyethylene and the like, and/or polymer materials such as polysulfone, polyether sulfone, polyacrylonitrile, polytetrafluoroethylene, polystyrene, polymethylmethacrylate, cellulose acetate, cellulose triacetate, regenerated cellulose, and the like.

The container 26 has an axial length which is capable of housing the respective hollow fibers 24 when the hollow fibers 24 are extended in a substantially linear shape. The container 26 is equipped with four terminals 28 (a first IC terminal 28a, a second IC terminal 28b, a first EC terminal 28c, and a second EC terminal 28d) that are connected respectively to the tubes 16. The first IC terminal 28a is provided at one end of the container 26 and communicates with the end space 26b on one end side. The second IC terminal 28b is provided at another end of the container 26 and communicates with the end space 26b on another end side. The first EC terminal 28c is provided on an outer peripheral surface of the container 26 in the vicinity of the other end side, and communicates with the main space 26a at a location in close proximity to the other end. The second EC terminal 28d is provided on an outer peripheral surface of the container 26 in the vicinity of the one end side, and communicates with the main space 26a at a location in close proximity to the one end.

The plurality of tubes 16 of the kit 12 include a cell solution tube 16A connected between the cell solution bag 18A and the cassette 10, a cleaning solution tube 16B connected between the cleaning solution bag 18B and the cassette 10, a culture medium tube 16C connected between the culture medium bag 18C and the cassette 10, a waste liquid tube 16D connected between the waste liquid bag 18D and the cassette 10, a collection tube 16E connected between the collection bag 18E and the cassette 10, a first IC tube 16F connected between the first IC terminal 28a of the bioreactor 21 and the cassette 10, a second IC tube 16G connected between the second IC terminal 28b of the bioreactor 21 and the cassette 10, a first EC tube 16H connected between the first EC terminal 28c of the bioreactor 21 and the cassette 10, and a second EC tube 16I connected between the second EC terminal 28d of the bioreactor 21 and the cassette 10.

Further, among the plurality of tubes 16, there are included closed tubes 16 that project from the cassette 10, together with being folded back and connected to the cassette 10 again. As such tubes 16, there are first, second, third, and fourth pump tubes 16J, 16K, 16L, and 16M, respectively, that are set on a plurality of (four) pumps 30 of the cell propagation device 15, and a sensor tube 16N that is set in an air bubble sensor 32 of the cell propagation device 15.

A gas exchanger 29 that mixes a predetermined gas component with a liquid (e.g., the culture medium) is provided at an intermediate position of the first EC tube 16H. As an example of the gas component to be mixed, there may be a gas component that approximates the mixing ratio of natural air (nitrogen N2: 75%, oxygen O2: 20%, and carbon dioxide CO2: 5%).

The structure of the gas exchanger 29 is not particularly limited, and in the same manner as the bioreactor 21, a structure can be supplied in which a plurality of hollow fibers 29b are provided inside a container 29a. More specifically, the gas exchanger 29 guides the liquid flowing through the first EC tube 16H into the internal cavities of the hollow fibers 29*b*, and during movement thereof inside the hollow fibers 29*b*, the gas component that is supplied to the interior of the container 29*a* (e.g., the space on the outer side of the hollow fibers 29*b*) is mixed with the liquid through the pores of the hollow fibers 29*b*.

In addition, by joining the aforementioned tubes 16 in advance, the cassette 10, which is one component of the kit 12, functions as a relay unit through which the cell solution, the cleaning solution, the culture solution, and the stripping solution of the respective medical bags 18 are allowed to flow to a different medical bag 18 or to the bioreactor 21. When the kit 12 is set in the cell propagation device 15, the cassette 10 is mounted in a cassette setting location (not shown) inside the cell propagation device 15, which simplifies the wiring operation of the tubes 16 in the propagation process.

Figure 2:
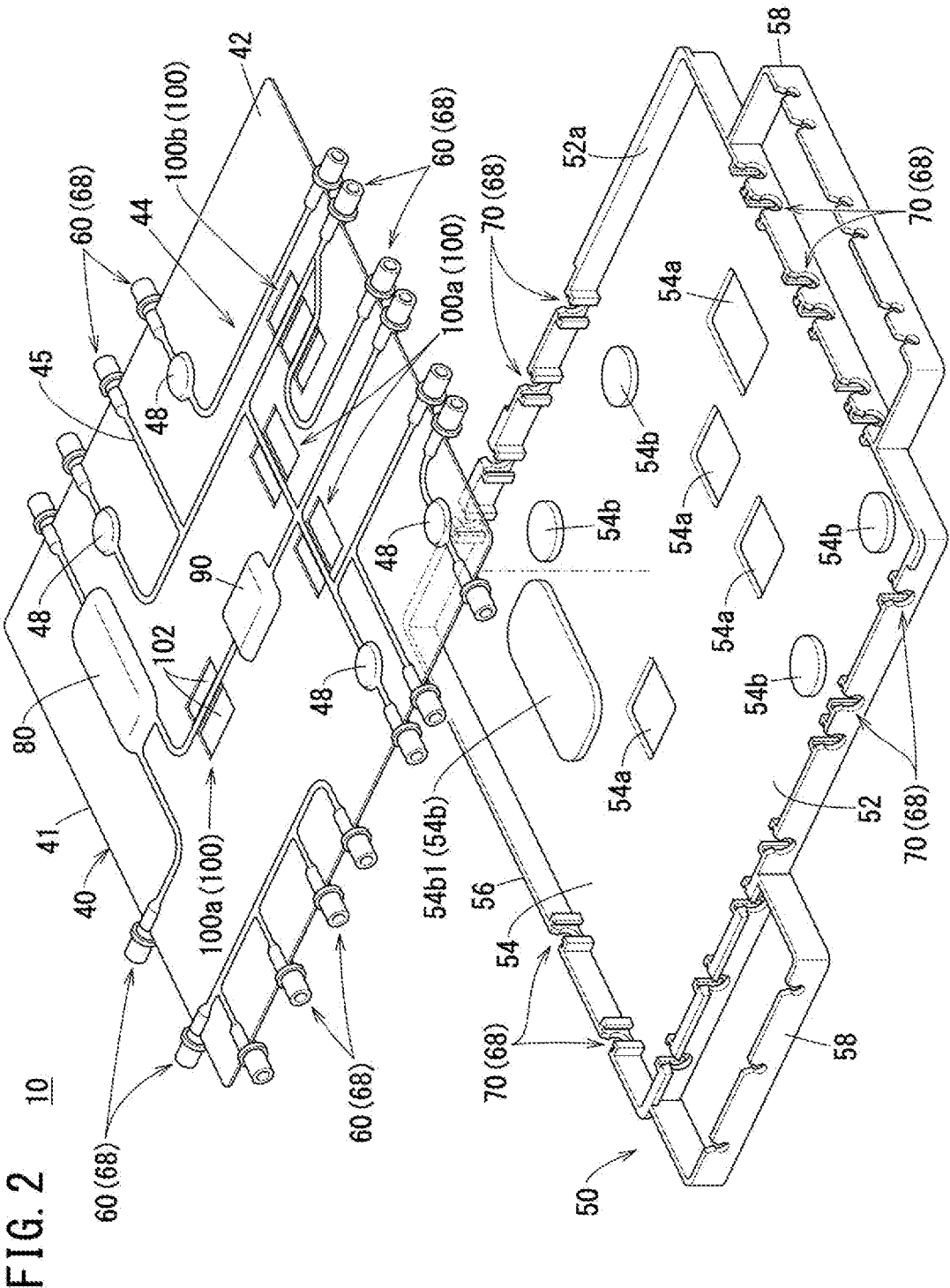
FIG. 2 is an exploded perspective view of the biological component cassette according to embodiments of the present disclosure.

As shown in FIG. 2, the cassette 10 comprises a soft cassette main body 40 to which the plurality of tubes 16 are directly connected, and a rigid frame 50 that retains the cassette main body 40 and is fixed to the cell propagation device 15.

The cassette main body 40 is substantially rectangular, or rectangular in shape, and is formed in a thin sheet shape which possesses flexibility. The cassette main body 40 is formed by stacking and joining (e.g., fusion bonding) together two resin sheets 42 made of a resin material in a thickness direction. In the fusion bonding of the pair of resin sheets 42, gas is supplied to and discharged between the pair of resin sheets 42 along grooves that are formed in a fusion bonding mold, whereby flow path walls 45, in which the resin sheets 42 are raised and project with semicircular shapes in cross-section, and flow paths 44 are formed on the inner sides thereof. The material forming the resin sheets 42 is not particularly limited, insofar as it possesses flexibility that is capable of being deformed by the pressure of the liquids, and for example, a vinyl chloride resin, a polyolefin resin, a polyurethane resin, or the like may be applied thereto. An embossing process may be implemented on the surface of the cassette main body 40, and fine convex/concave irregularities may be formed therein. A plurality of connectors 60 for connection between the plurality of tubes 16 and the flow paths 44 are provided on outer edges 41 of the cassette main body 40.

On the other hand, the frame 50 comprises a resin material that is harder (e.g., having a greater modulus of elasticity, increased rigidity, etc.) and/or more rigid than the cassette main body 40, and is formed in the shape of a thin concave portion having an accommodation space 52 therein in which the cassette main body 40 is accommodated. The constituent material of the frame 50 is not limited to any particular material, and examples of materials used may include a thermoplastic resin material such as polypropylene, polycarbonate, polyamide, polysulfone, polyarylate, methacrylate-butylene-styrene copolymer, or the like.

The frame 50 includes a substantially rectangular shaped cover member 54 which is slightly larger than the cassette main body 40, and side portions 56 that project a short distance from the outer periphery of the cover member 54 in a direction perpendicular to the cover member 54. The side portions 56 extend around the entire outer periphery of the cover member 54. In the frame 50, the accommodation space 52 is opened through an opening 52*a* surrounded by the side portions 56 on an opposite side from the cover member 54, thereby allowing one surface of the cassette main body 40 to be exposed. Engaging portions 70 in which the respective connectors 60 are arranged and retained are provided in the side portions 56 at positions corresponding to each of the connectors 60 of the cassette main body 40. The connectors 60 and the engaging portions 70 constitute engagement mechanisms 68 for engagement with the cassette main body 40.

Figure 3:
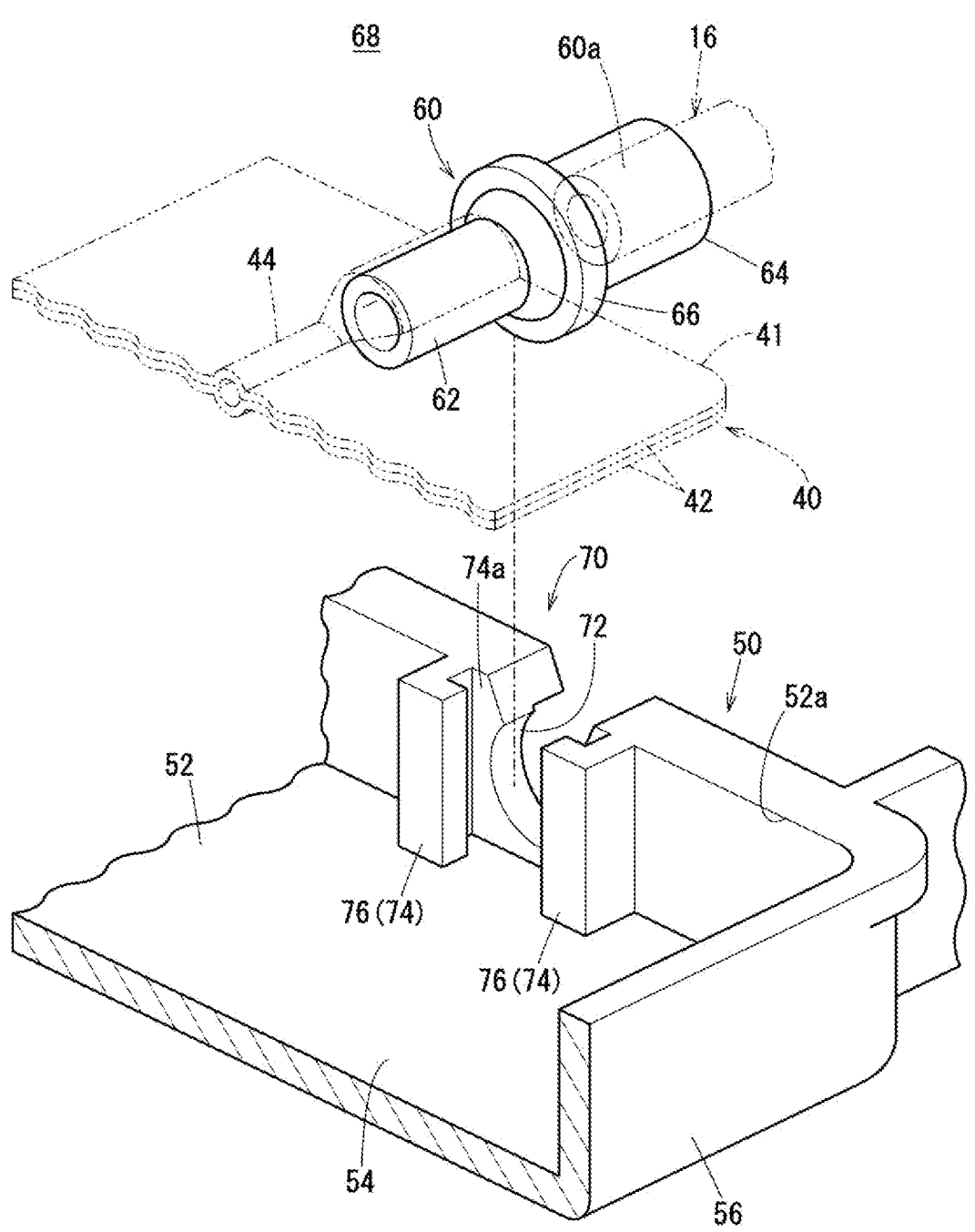
FIG. 3 is a partially enlarged perspective view of an engagement mechanism of the biological component cassette according to embodiments of the present disclosure.

As shown in FIG. 3, each of the connectors 60 of the cassette main body 40 includes a first cylindrical part 62 that is sealed to the cassette main body 40, a second cylindrical part 64 connected to the tube 16, and a flange 66 that projects radially outward between the first cylindrical part 62 and the second cylindrical part 64. Further, a communication hole 60*a* that penetrates through the first cylindrical part 62, the second cylindrical part 64, and the flange 66 is formed in the axial center of the connector 60.

At a time of sealing, when the two resin sheets 42 of the cassette main body 40 are placed together and sealed, the first cylindrical parts 62 are fusion bonded to the cassette main body 40, in a state in which the communication holes 60*a* communicate with the flow paths 44 of the cassette 10. An outer circumferential surface of the first cylindrical parts 62 is formed with a smaller diameter than the second cylindrical parts 64 in order to correspond with the flow paths 44 of the cassette 10. Further, the tubes 16 are inserted inside the second cylindrical parts 64, and are firmly fixed to the second cylindrical parts 64 by an appropriate fixing means. The flanges 66 have a predetermined thickness in the axial direction of the connectors 60, and are formed in a ring shape that encircles the entire outer peripheral surface of the connectors 60.

On the other hand, the engaging portions 70 of the frame 50 include engagement recesses 72 in which the side portions 56 are cut out, and movement limiters 74 that project from the side portions 56 toward the inner side of the frame 50 in close proximity to the engagement recesses 72. The engagement recesses 72 are opened in the same direction as the opening 52*a* of the frame 50, and are formed in arcuate shapes (e.g., C-shapes) which are capable of accommodating the tubes 16 connected to the connectors 60 (e.g., second cylindrical parts 64). The engagement recesses 72 are set to a size that enables them to be firmly fitted with respect to the accommodated tubes 16 and the connectors 60.

Each of the movement limiters 74 is constituted by a pair of hook portions 76 which project inwardly from the inner surface of the side portions 56, and are bent in perpendicular directions and in directions to approach mutually toward each other. In addition, the movement limiters 74 allow the flanges 66 of the connectors 60 to be accommodated in fixed spaces 74*a* formed between the movement limiters 74 and the side portions 56.

Movement of the connectors 60 in the axial direction is restricted by disposing the flanges 66 in the fixed spaces 74*a*. Further, the connectors 60 are accommodated in the engagement recesses 72 together with the tubes 16, whereby the connectors 60 become engaged with the engaging portions 70 (e.g., side portions 56) at an appropriate engagement force, and the connectors 60 are prevented from slipping out from the frame 50. By the respective connectors 60 of the cassette main body 40 being retained by the respective engaging portions 70 of the frame 50, the cassette 10 becomes placed in a state in which the cassette main body 40 and the frame 50 are integrated (e.g., placed in a state in which the cassette main body 40 and the frame 50 can be handled together collectively).

Returning to FIG. 2, the aforementioned engagement mechanisms 68 are disposed respectively on four sides of the substantially rectangular shaped cassette 10. More specifically, the cassette main body 40 is equipped with the connectors 60 at each of four outer edges 41, whereas the frame 50 is also equipped with the engaging portions 70 at each of four side portions 56. Consequently, the frame 50 retains the sheet-shaped cassette main body 40 in a stretched state, and is capable of suitably causing the flow paths 44 to be extended along a planar direction.

The cover member 54 of the frame 50 includes a plurality of windows 54a (e.g., four windows, etc.) and a plurality of convex portions 54b (e.g., five convex portions, etc.) corresponding to the constitution of the cassette main body 40 that is retained therein. The plurality of windows 54a are provided at positions facing toward flow path opening/closing units 100, to be described later. The windows 54a are formed in rectangular shapes, for example, to match the shape of cutouts 102 of the flow path opening/closing units 100. The convex portions 54b are disposed at positions facing toward pressure target detection units 48 and a liquid level target detection unit 80, to be described later. One convex portion 54b1 from among the plurality of convex portions 54b is formed in a substantially rectangular shape corresponding to the shape of the liquid level target detection unit 80.

In addition, the cassette 10 is set inside the cell propagation device 15 in which the cassette main body 40 and the frame 50 are integrated, and the planar direction of the cassette main body 40 is set in an upright posture along the direction of gravity (e.g., in the vertical direction). More specifically, in the interior of the cell propagation device 15, the cassette 10 is fixed to the cassette setting location of the cell propagation device 15 while being oriented in the vertical direction shown in FIG. 4. Moreover, the cassette 10 in FIG. 4 is shown in a posture as viewed from the side of the cover member 54 (e.g., the side of a touch panel 134 of the cell propagation device 15) in a state of being mounted in the cell propagation device 15, and in order to simplify description, the frame 50 is omitted and only the cassette main body 40 is shown.

Figure 4:
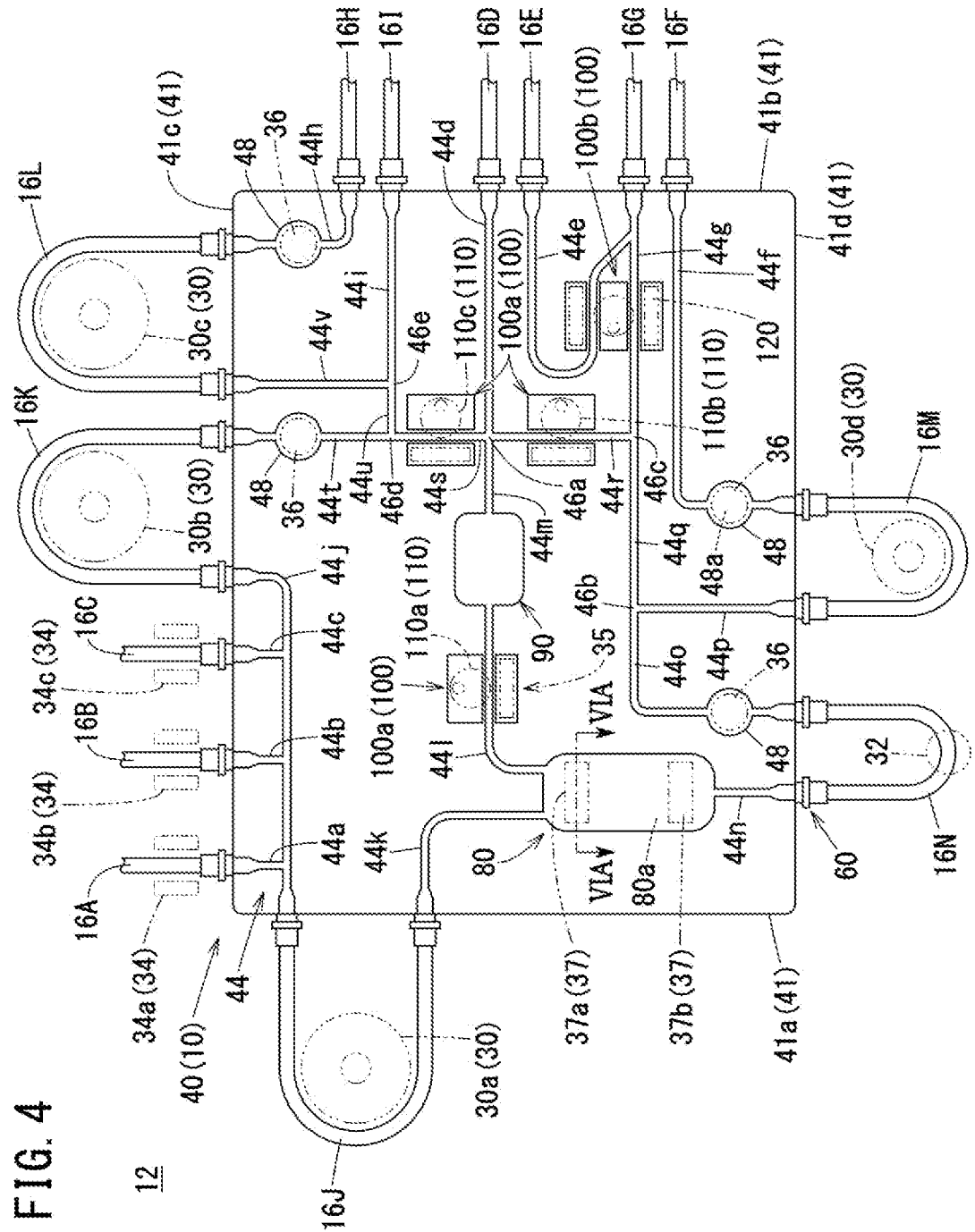
FIG. 4 is a plan view showing a cassette main body and a peripheral portion thereof according to embodiments of the present disclosure.

More specifically, the outer edges 41 of the cassette main body 40 may include a first short side 41a (left side), a second short side 41b (right side), a first long side 41c (upper side), and a second long side 41d (lower side), as illustrated in FIG. 4. The cell solution tube 16A, the cleaning solution tube 16B, and the culture medium tube 16C are connected to the first long side 41c. The waste liquid tube 16D, the collection tube 16E, the first IC tube 16F, the second IC tube 16G, the first EC tube 16H, and the second EC tube 16I are connected to the second short side 41b.

Figure 5:
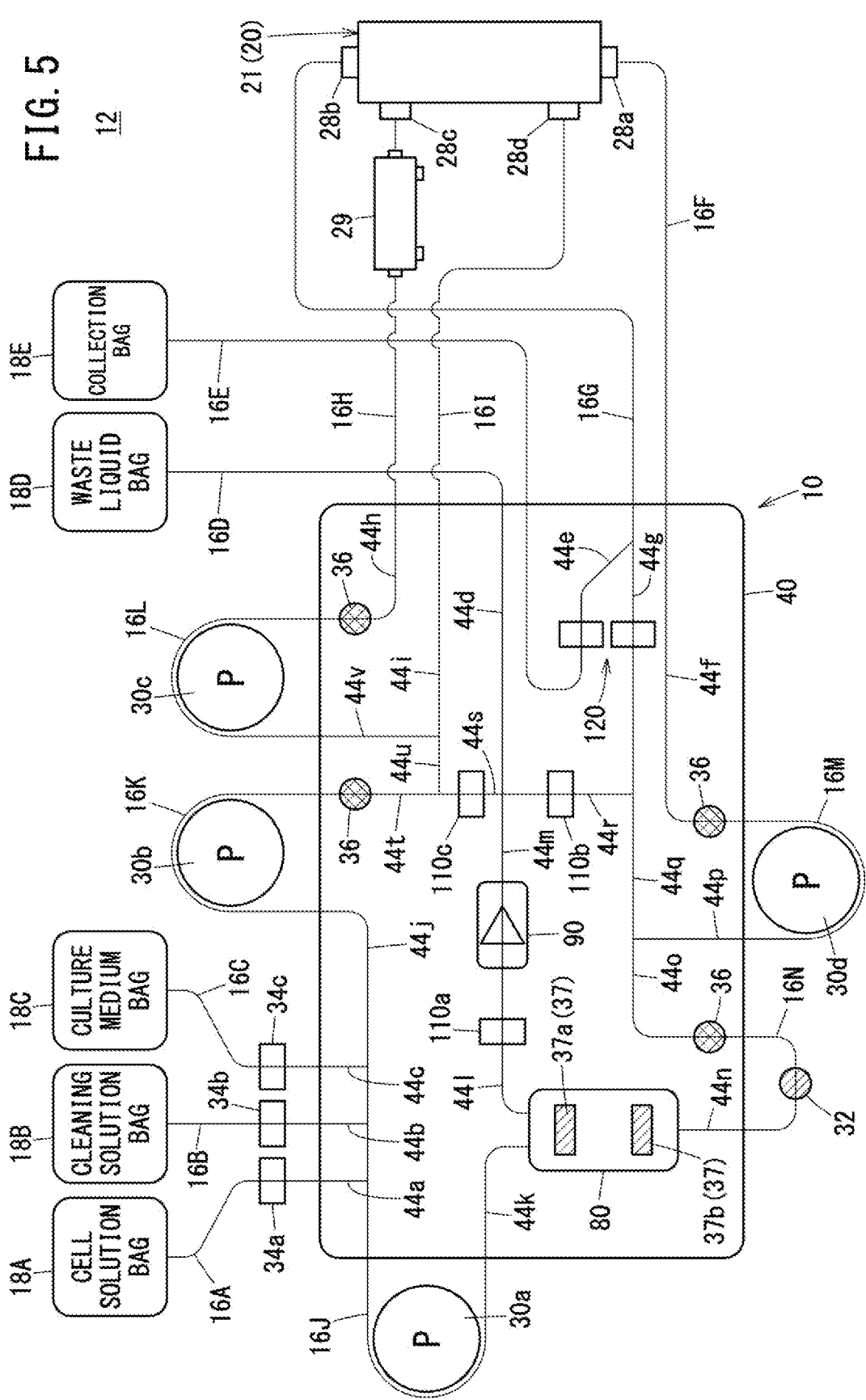
FIG. 5 is a schematic diagram showing liquid pathways of the biological component kit according to embodiments of the present disclosure.

Further, as shown in FIGS. 4 and 5, in the cell propagation system 23, in the set state, four pumps 30 are arranged at positions in close proximity to the sides of the cassette 10. In the set state, the cell propagation device 15 includes a first pump 30a disposed in close proximity to the first short side 41a, a second pump 30b and a third pump 30c disposed in close proximity to the first long side 41c, and a fourth pump 30d disposed in close proximity to the second long side 41d. The first pump 30a causes the liquid to flow in an IC route, and the second pump 30b causes the liquid to flow in an EC route. Further, the third pump 30c circulates the liquid of the EC route, and the fourth pump 30d circulates the liquid of the IC route.

Therefore, in the kit 12 (and correspondingly in the cassette 10), the first pump tube 16J is connected to the first short side 41a, the second pump tube 16K and the third pump tube 16L are connected to the first long side 41c, and the fourth pump tube 16M is connected to the second long side 41d, respectively. The first to fourth pump tubes 16J to 16M are arranged in a manner so that the portions thereof that are folded back in an arcuate shape are wrapped around circular shaped wound portions of the first to fourth pumps 30a to 30d. By being rotated in a squeezing manner around the respective wrapped around first to fourth pump tubes 16J to 16M, the first to fourth pumps 30a to 30d apply a fluid force to the liquids inside the first to fourth pump tubes 16J to 16M.

Furthermore, in the cell propagation system 23, in the set state, the air bubble sensor 32 is arranged at a position in the vicinity of the second long side 41d of the cassette main body 40. Therefore, in the kit 12, the sensor tube 16N is connected to the second long side 41d, and the sensor tube 16N is arranged in facing relation to the air bubble sensor 32. The air bubble sensor 32 is not particularly limited, but for example, there may be applied thereto an ultrasonic sensor or the like that sandwiches the sensor tube 16N between a pair of non-illustrated inspection walls, and which transmits ultrasonic waves between the inspection walls.

In addition, in the cell propagation system 23, in the set state, a plurality of outer side clamps 34 are arranged in close proximity to the side of the cassette 10, together with a plurality of inner side clamps 35 being arranged on the inner side of the cassette 10. More specifically, in the set state, the plurality of outer side clamps 34 include a first outer side clamp 34a in which the cell solution tube 16A is disposed, a second outer side clamp 34b in which the cleaning solution tube 16B is disposed, and a third outer side clamp 34c in which the culture medium tube 16C is disposed. Under the control of the cell propagation device 15, by sandwiching the respective tubes 16, the first to third outer side clamps 34a to 34c act to close the flow paths of the respective tubes 16, while on the other hand, the respective tubes 16 are retained in a state in which the flow paths are opened. The constitution of the plurality of inner side clamps 35 will be described in detail together with the configuration of the cassette main body 40.

The frame 50 of the cassette 10 includes a retaining frame 58 that extends outwardly from the upper side and the right side of the side portions 56, for example, as shown in FIG. 2, and retains the tubes 16 which are separated a predetermined distance from the side portions 56. The retaining frame 58 provided on the upper side retains the cell solution tube 16A, the cleaning solution tube 16B, and the culture medium tube 16C, thereby making it possible to suitably open and close the flow paths of the tubes 16 by each of the outer side clamps 34.

The cassette 10 (e.g., the cassette main body 40), in addition to being equipped with the above-described flow paths 44, comprises the plurality of pressure target detection units 48, the liquid level target detection unit 80, and a check valve unit 90 in communication with the flow paths 44, and the plurality of flow path opening/closing units 100 disposed with the flow paths 44.

The flow paths 44 of the cassette main body 40 include a cell solution port path 44a in communication with the cell solution tube 16A, a cleaning solution port path 44b in communication with the cleaning solution tube 16B, a culture medium port path 44c in communication with the culture medium tube 16C, a waste liquid port path 44d in communication with the waste liquid tube 16D, a collection port path 44e in communication with the collection tube 16E, a first IC port path 44f providing communication between the first IC tube 16F and the other end of the fourth pump tube 16M, a second IC port path 44g in communication with the second IC tube 16G, a first EC port path 44h providing communication between the first EC tube 16H and the other end of the third pump tube 16L, a second EC port path 44i in communication with the second EC tube 16I, a first path 44*j* providing communication between one end of the first pump tube 16J and one end of the second pump tube 16K, a second path 44*k* providing communication between the other end of the first pump tube 16J and the liquid level target detection unit 80, a third path 44*l* providing communication between the liquid level target detection unit 80 and the check valve unit 90, a fourth path 44*m* providing communication between the check valve unit 90 and a connection point 46*a*, a fifth path 44*n* providing communication between the liquid level target detection unit 80 and one end of the sensor tube 16N, a sixth path 44*o* providing communication between the other end of the sensor tube 16N and a connection point 46*b*, a seventh path 44*p* providing communication between one end of the fourth pump tube 16M and the connection point 46*b*, an eighth path 44*q* providing communication between the connection point 46*b* and a connection point 46*c*, a ninth path 44*r* providing communication between the connection point 46*a* and the connection point 46*c*, a tenth path 44*s* providing communication between the connection point 46*a* and a connection point 46*d*, an eleventh path 44*t* providing communication between the connection point 46*d* and the other end of the second pump tube 16K, a twelfth path 44*u*, providing communication between the connection point 46*d* and a connection point 46*e*, and a thirteenth path 44*v* providing communication between the connection point 46*e* and one end of the third pump tube 16L.

More specifically, the waste liquid port path 44*d*, the fourth path 44*m*, the ninth path 44*r*, and the tenth path 44*s* are connected to the connection point 46*a*. The sixth path 44*o*, the seventh path 44*p*, and the eighth path 44*q* are connected to the connection point 46*b*. The second IC port path 44*g*, the eighth path 44*q*, and the ninth path 44*r* are connected to the connection point 46*c*. The tenth path 44*s*, the eleventh path 44*t*, and the twelfth path 44*u* are connected to the connection point 46*d*. The second EC port path 44*i*, the twelfth path 44*u*, and the thirteenth path 44*v* are connected to the connection point 46*e*. Further, the first path 44*j* has a non-illustrated confluence point where the cell solution port path 44*a*, the cleaning solution port path 44*b*, and the culture medium port path 44*c* are connected respectively to each other. The second IC port path 44*g* also includes a non-illustrated confluence point to which the collection port path 44*e* is connected. At the connection points 46*a* to 46*e* and the confluence points, the flow paths 44 that are connected communicate with each other, whereby the liquid in one of such flow paths 44 flows smoothly into the other flow paths 44 without the occurrence of stagnation.

The biological component cassette 10 having the above-described flow paths 44 includes in an integrated fashion the IC route for supplying liquid to the internal cavities of the hollow fibers 24 during the propagation process, and the EC route for supplying liquid to the outer sides (e.g., the main space 26*a*) of the hollow fibers 24. The IC route is primarily constituted by the first IC port path 44*f*, the second IC port path 44*g*, and the second path 44*k* to the ninth path 44*r*. Further, the IC route has a circulation circuit in which liquid is circulated between the cassette main body 40 and the bioreactor 21, and the circulation circuit inside the cassette main body 40 is constituted by the first IC port path 44*f*, the second IC port path 44*g*, the seventh path 44*p*, and the eighth path 44*q*. On the other hand, the EC route is primarily constituted by the first EC port path 44*h*, the second EC port path 44*i*, and the tenth path 44*s* to the thirteenth path 44*v*. Further, the EC route has a circulation circuit in which liquid is circulated between the cassette main body 40 and the bioreactor 21, and the circulation circuit inside the cassette main body 40 is constituted by the first EC port path 44*h*, the second EC port path 44*i*, and the thirteenth path 44*v*.

When the cassette main body 40 is viewed in plan, the plurality of pressure target detection units 48 of the cassette main body 40 are formed so as to be spread out in a planar direction and in substantially circular shapes with respect to the continuously disposed flow paths 44. Each of the pressure target detection units 48 includes a flow through chamber 48*a* through which liquid flows between the pair of resin sheets 42, and based on the liquid that has flowed into the flow through chamber 48*a*, the pressure target detection units 48 bulge out and are restored to their original state in directions perpendicular to the planar direction of the resin sheets 42 (e.g., in the thickness direction of the cassette main body 40). The respective pressure target detection units 48 are arranged at positions facing toward pressure sensors 36 provided in the cell propagation device 15.

The pressure sensors 36 of the cell propagation device 15 are not particularly limited, and the pressure sensors may be used in various ways. For example, the pressure sensors 36 cooperate with the frame 50 (the cover member 54) of the cassette 10 to sandwich the pressure target detection units 48 therebetween, and detection devices (e.g., magnetic sensors) that detect the amount of deformation of the pressure target detection units 48 that have been expanded by the liquid can be used.

On the other hand, the liquid level target detection unit 80 is disposed at one location inside the cassette main body 40, and is capable of detecting a liquid level of the liquid that flows through the liquid level target detection unit 80. The liquid level target detection unit 80 includes a storage space 80*a* in which the liquid is temporarily stored in the interior (e.g., between the pair of resin sheets 42) thereof. The second path 44*k* and the third path 44*l* are individually connected in communication with an upper end of the storage space 80*a*, whereas the fifth path 44*n* is connected in communication with a lower end of the storage space 80*a*.

Further, when the cassette main body 40 is viewed from the front, the liquid level target detection unit 80 is formed in a rectangular shape with four rounded corners. The longitudinal direction of the liquid level target detection unit 80 lies along the direction of gravity in the set state of the cassette main body 40. The length in the longitudinal direction of the liquid level target detection unit 80 is preferably formed to be greater than or equal to two times the length in the lateral direction of the liquid level target detection unit 80.

Figure 6A:
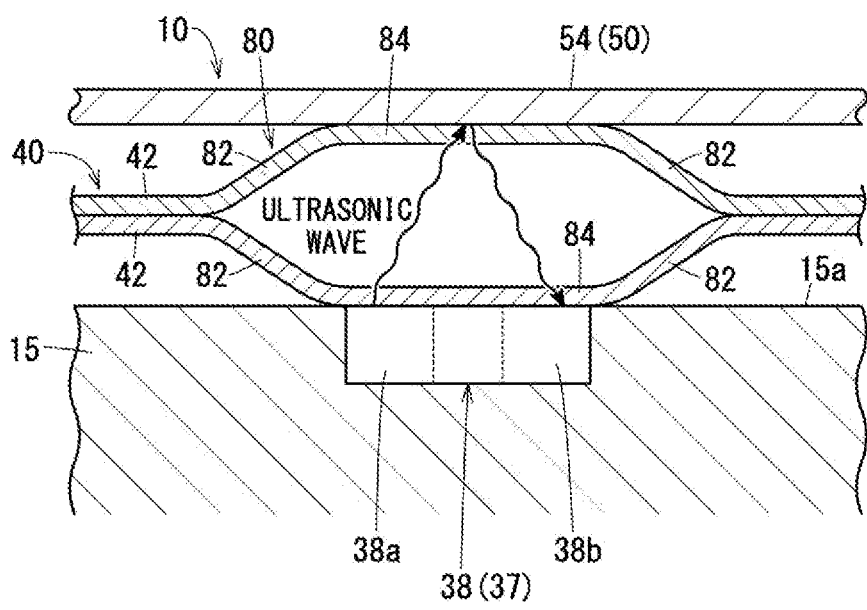
FIG. 6A is a schematic cross-sectional view of a portion corresponding to line VIA-VIA in FIG. 4 showing an ultrasonic sensor of the biological component treatment system according to embodiments of the present disclosure.

In the cross-sectional view shown in FIG. 6A, the liquid level target detection unit 80 includes outer peripheral portions 82 that smoothly rise from a fusion bonded portion of the pair of resin sheets 42, and flat portions 84 that are formed in flat shapes on the inner side of the outer peripheral portions 82. The flat portions 84 are constituted in a manner so as to maintain parallelism between the pair of resin sheets 42, and the flat portions 84 are arranged in facing relation to a liquid level sensors 37 in the set state. A cross-sectional area of a location in the storage space 80*a* in which the liquid is stored is sufficiently greater (e.g., two times greater or more than two times greater) than the cross-sectional area of the flow paths 44. In the liquid level target detection unit 80, the liquid level rises when the inflowing amount of the liquid flowing into the storage space 80*a* exceeds the outflowing amount, whereas the liquid level decreases when the inflowing amount falls below the outflowing amount of the liquid from the storage space 80*a*.

The liquid level sensors 37 provided in the cell propagation device 15 include an upper sensor 37*a* that detects an upper limit position, and a lower sensor 37b that detects a lower limit position of the liquid level in the storage space 80a. More specifically, the cell propagation system 23 is configured such that, by detecting the upper limit position and the lower limit position at the time that the liquid is stored, air is discharged from the liquid while the amount of liquid stored in the liquid level target detection unit 80 is adjusted. Further, the upper and lower sensors 37a and 37b face toward the flat portions 84 in the set state, and are capable of stably detecting the liquid level. Although the type of the liquid level sensors 37 is not particularly limited, an ultrasonic sensor 38 (see FIG. 6A) or a capacitance sensor 39 (see FIG. 6B) may be applied thereto.

For example, as shown in FIG. 6A, on an arrangement surface 15a on which the liquid level target detection unit 80 is arranged, the ultrasonic sensor 38 is provided with an oscillating unit 38a that outputs ultrasonic waves, and a receiving unit 38b that detects the ultrasonic waves. More specifically, for the ultrasonic sensor 38, a reflection type that utilizes the frame 50 of the cassette 10 is applied. In this case, the ultrasonic sensor 38 causes the ultrasonic waves that are oscillated from the oscillating unit 38a to be reflected at the cover member 54 (e.g., wall portion), and detects the reflected waves at the receiving unit 38b. Moreover, the arrangement surface 15a and the cover member 54 are constituted in a manner so as to form a state in which the cassette main body 40 (e.g., each of the pair of resin sheets 42) is placed in contact therewith accompanying setting of the cassette 10.

In addition, it is preferable for the cassette 10 to be in a state in which the liquid level target detection unit 80 is in contact with the cover member 54 (e.g., the convex portion 54b1) in advance. Further, for example, the resin sheets 42 that constitute the liquid level target detection unit 80 may be fixed to the cover member 54. Further, the ultrasonic sensor 38 may be configured so as to project from the arrangement surface 15a in order to be placed in contact with the liquid level target detection unit 80. Further, the cover member 54 may project out toward the ultrasonic sensor 38 in order to be placed in contact with the liquid level target detection unit 80.

Figure 6B:
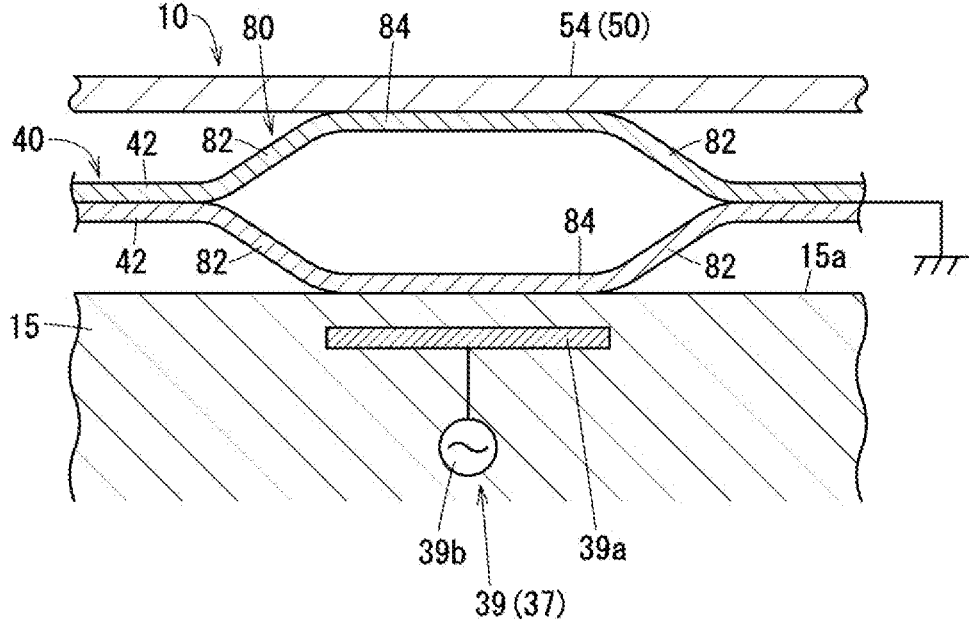
FIG. 6B is a schematic cross-sectional view showing a capacitance sensor of the biological component treatment system according to embodiments of the present disclosure.
Figure 7A:
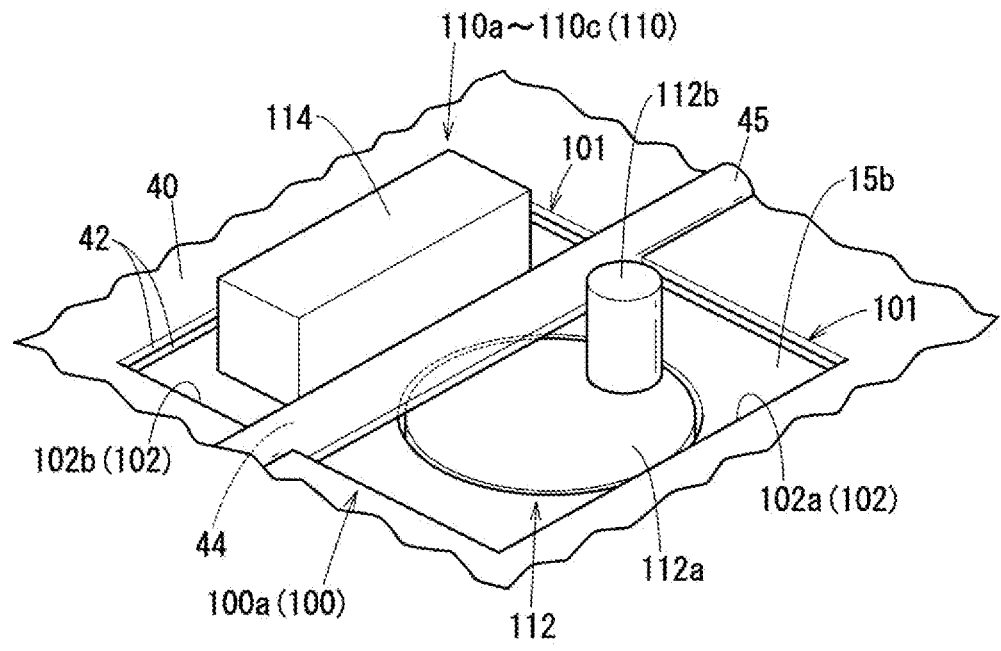
FIG. 7A is an enlarged perspective view showing a single flow path opening/closing unit and an opened state of a flow path of a single clamp structure according to embodiments of the present disclosure.
Figure 7B:
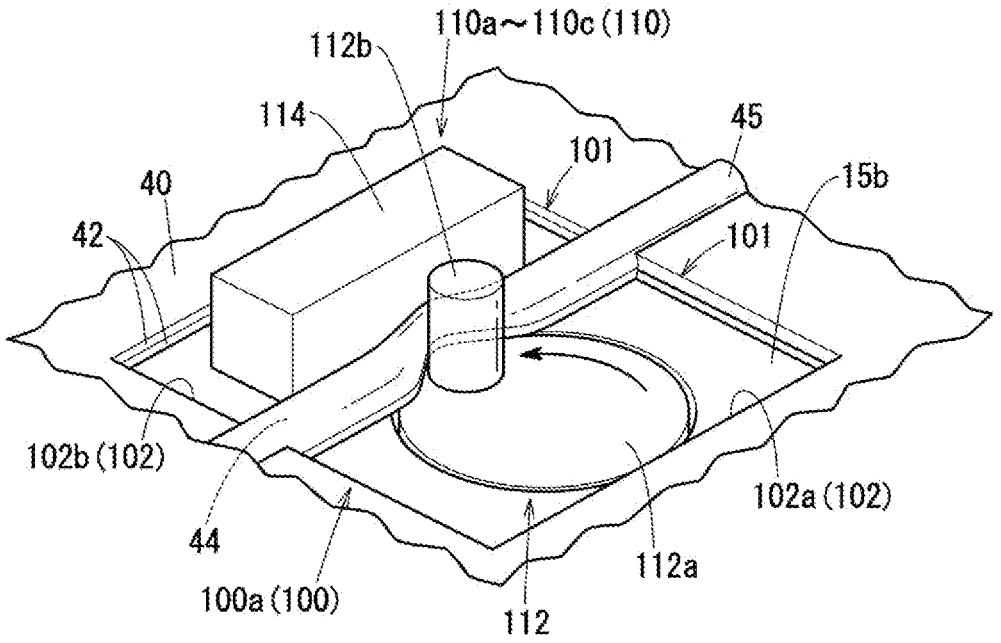
FIG. 7B is an enlarged perspective view showing the single flow path opening/closing unit and a closed state of the flow path of the single clamp structure according to embodiments of the present disclosure.

Alternatively, as shown in FIG. 6B, the capacitance sensor 39 is equipped with a flat plate 39a in the arrangement surface 15a on which the liquid level target detection unit 80 is arranged, together with being equipped with an AC power source 39b that is electrically connected to the flat plate 39a. More specifically, since it can be said that the liquid level target detection unit 80 of the cassette main body 40 is grounded via the frame 50 and the cell propagation device 15, a capacitance is generated between the liquid level target detection unit 80 and the flat plate 39a to which AC power is supplied from the AC power source 39b. The capacitance changes depending on whether a gas or a liquid exists within the storage space 80a that faces toward the flat plate 39a, and therefore, by the capacitance sensor 39 detecting such a change in capacitance, it is possible to detect the level of the liquid that is stored in the storage space 80a.

Moreover, in the case that capacitance sensors 39 are used as the liquid level sensors 37, the liquid level target detection unit 80 may be disposed in a slightly spaced apart manner without being placed in contact with the arrangement surface 15a. This is because, even if separated in this manner, the capacitance sensors 39 are still capable of detecting the change in capacitance due to a difference between the liquid and the gas. Further, a surface of the liquid level target detection unit 80 may be subjected to embossing or the like to form fine concave/convex irregularities thereon.

Returning to FIG. 5, the check valve unit 90 of the cassette main body 40 has a function of allowing a fluid (e.g., a liquid and/or a gas) to flow in a first direction (e.g., the rightward direction in FIG. 5), while blocking flow of the fluid in a second direction that is an opposite direction to the first direction (e.g., the leftward direction in FIG. 5). Although the composition of the check valve unit 90 is not particularly limited, the check valve unit 90 can be constructed by overlaying a valve structure (e.g., a structure in which two sheets for the valve that become narrower toward the first direction are joined, and form openings at both ends in the first and second directions) between the pair of resin sheets 42.

On the other hand, the plurality of flow path opening/closing units 100 are created by forming cutouts 102 (e.g., sheet separating portions 101) at adjacent positions in directions on both sides (e.g., the widthwise direction) perpendicular to the direction in which the flow paths 44 extend. Further, in some embodiments, the respective flow path opening/closing units 100 include single flow path opening/closing units 100a provided in the third path 44l, the ninth path 44r, and the tenth path 44s, and a multiple flow path opening/closing unit 100b provided to span across the collection port path 44e and the second IC port path 44g.

The single flow path opening/closing units 100a are constituted by forming a first cutout 102a and a second cutout 102b on both sides of each of the flow paths 44. More specifically, concerning the respective flow paths 44 of the single flow path opening/closing units 100a, the outer circumferential surfaces (e.g., the cylindrically shaped flow path walls 45) of the flow paths 44 are separated over the entire circumference thereof with respect to the resin sheets 42 by the sheet separating portions 101 (e.g., the first cutout 102a and the second cutout 102b). The first and second cutouts 102a and 102b are formed respectively in rectangular shapes, and are provided so as to sandwich mutually therebetween the flow path walls 45 that constitute the flow paths 44. The length in the widthwise direction (e.g., a lateral direction) of the first cutout 102a is longer than the length in the widthwise direction of the second cutout 102b. Further, the first cutout 102a and the second cutout 102b are set with the same length in the longitudinal direction. It should be noted that the shapes of the cutouts 102 are not particularly limited, and various shapes can be adopted therefor.

In the cell propagation device 15, in a state in which the cassette 10 is set therein, single clamp structures 110 that constitute the inner side clamps 35 are arranged respectively in the plurality of single flow path opening/closing units 100a. Hereinafter, the one that is arranged on the third path 44l may also be referred to as a first single clamp structure 110a, the one that is arranged on the ninth path 44r may also be referred to as a second single clamp structure 110b, and the one that is arranged on the tenth path 44s may also be referred to as a third single clamp structure 110c. Each of the respective single clamp structures 110 is equipped with a rotating body 112 (e.g., a rotating member) disposed on an arrangement surface 15b, and a fixed body 114 that projects a short distance from the arrangement surface 15b.

The rotating body 112 includes a disk portion 112a that faces toward both the flow path 44 and the first cutout 102a, and one pin 112b (e.g., displacement body) disposed in close proximity to an outer circumferential edge of the disk portion 112a. The disk portion 112a rotates about a center point under the control of the cell propagation device 15, and causes the pin 112b to be brought into close proximity to and separated away from the fixed body 114. When set, the pin 112b is inserted into the first cutout 102a at a position separated from the fixed body 114 to a certain extent.

The fixed body 114 is formed in a rectangular block shape that can be inserted into the second cutout 102b, and projects at a height that is shorter than the side portions 56 of the frame 50. The fixed body 114, by cooperating with the rotating body 112, realizes opening and closing of each of the flow paths 44. More specifically, accompanying rotation of the rotating body 112, when the pin 112b is closest in proximity to the fixed body 114, the single clamp structure 110 crushes the flow path wall 45 between the pin 112b and the fixed body 114, and closes the flow path 44.

Further, the multiple flow path opening/closing unit 100b selectively opens and closes two flow paths 44 (e.g., the collection port path 44e, and the second IC port path 44g) that lie in parallel adjacent to each other, and therefore, is constituted by a first cutout 103a, a second cutout 103b, and a third cutout 103c. More specifically, the first cutout 103a is disposed between the collection port path 44e and the second IC port path 44g. Further, the second cutout 103b is disposed on the other side of the second IC port path 44g (the side opposite from the first cutout 103a), and the third cutout 103c is provided on the other side of the collection port path 44e (the side opposite from the first cutout 103a).

In the respective flow paths 44 of the multiple flow path opening/closing unit 100b as well, the outer circumferential surfaces (e.g., the cylindrically shaped flow path walls 45) of the flow paths 44 are separated over the entire circumference thereof with respect to the resin sheets 42 by the sheet separating portions 101 (the first cutout 103a, the second cutout 103b, and the third cutout 103c). The first to third cutouts 103a to 103c are formed respectively in rectangular shapes, and are provided so as to sandwich mutually therebetween the flow path walls 45 that constitute the respective flow paths 44. The length in the widthwise direction (e.g., the lateral direction) of the first cutout 103a is longer than the length in the widthwise direction of the second and third cutouts 103b and 103c. Further, the first to third cutouts 103a to 103c are set with the same length in the longitudinal direction.

On the other hand, in the cell propagation device 15, in a state in which the cassette 10 is set therein, a switchable clamp structure 120 that constitutes one of the inner side clamps 35 is arranged with respect to the multiple flow path opening/closing unit 100b. The switchable clamp structure 120 is equipped with a rotating body 122 provided on the arrangement surface 15b and a plurality of fixed bodies 124 (e.g., two) that project from the arrangement surface 15b.

The rotating body 122, similar to the above-described rotating body 112, includes a disk portion 122a, and one pin 122b (e.g., displacement body) disposed in close proximity to an outer circumferential edge of the disk portion 122a. The disk portion 122a is arranged in facing relation to the two flow paths 44 (e.g., the collection port path 44e and the second IC port path 44g) and the first cutout 103a. The disk portion 122a rotates about a center point under the control of the cell propagation device 15, and causes the pin 122b to be brought into close proximity to and separated away from the two fixed bodies 124. When set, the pin 122b is inserted into the first cutout 103a.

One from among the two fixed bodies 124 is inserted into the second cutout 103b, and the other is inserted into the third cutout 103c. When the pin 122b is closest in proximity to one of the fixed bodies 124 (e.g., the one in the third cutout 103c), the switchable clamp structure 120 closes the flow path 44 (e.g., the collection port path 44e) by crushing the flow path wall 45 between the pin 122b and the fixed body 124. At this time, the opposite flow path 44 (the second IC port path 44g) is opened. Further, when the pin 122b is closest in proximity to the other fixed body 124, the switchable clamp structure 120 closes the second IC port path 44g, while on the other hand, opens the collection port path 44e.

Returning to FIG. 1, the cell propagation device 15 in which the kit 12 is mounted is equipped with a box-shaped device main body 130, and a stand 132 on which the respective medical bags 18 of the kit 12 are retained. Further, the touch panel 134 (display operation unit) for carrying out operations and displays when the propagation process is performed is provided on an outer surface of the device main body 130. Furthermore, in the interior of the device main body 130, there are provided a cassette placement unit (not shown) in which the cassette 10 is fixed in an upright posture, and further, the bioreactor 21 is retained at an appropriate height, and a control unit 136 that controls operation of the cell propagation system 23. Although illustration thereof is omitted, it goes without saying that the cell propagation device 15 may include a functional unit for realizing various conditions that are required for culturing the cells. For example, the cell propagation device 15 may be equipped with a temperature adjustment unit that executes a temperature control to maintain the culturing environment at 37° C.

Next, operations of the tubes 16 and the flow paths 44 of the cassette 10 in the propagation process of the cell propagation system 23 will be discussed.

As shown in FIG. 1, in the propagation process of the cell propagation system 23, the operator inserts portions of the kit 12 including the cassette 10 into the cell propagation device 15. Further, the operator places the appropriate tubes 16 of the kit 12 on the pumps 30, the air bubble sensor 32, and the outer side clamps 34 of the cell propagation device 15, together with placing the flow path opening/closing units 100 on the inner side clamps 35. Consequently, as shown in FIGS. 4 and 5, the cassette 10 is set in the cell propagation device 15 with the planar direction thereof being oriented in a posture along the direction of gravity. Furthermore, the respective medical bags 18 of the kit 12 are also suspended from the stand 132 by the operator.

Figure 9:
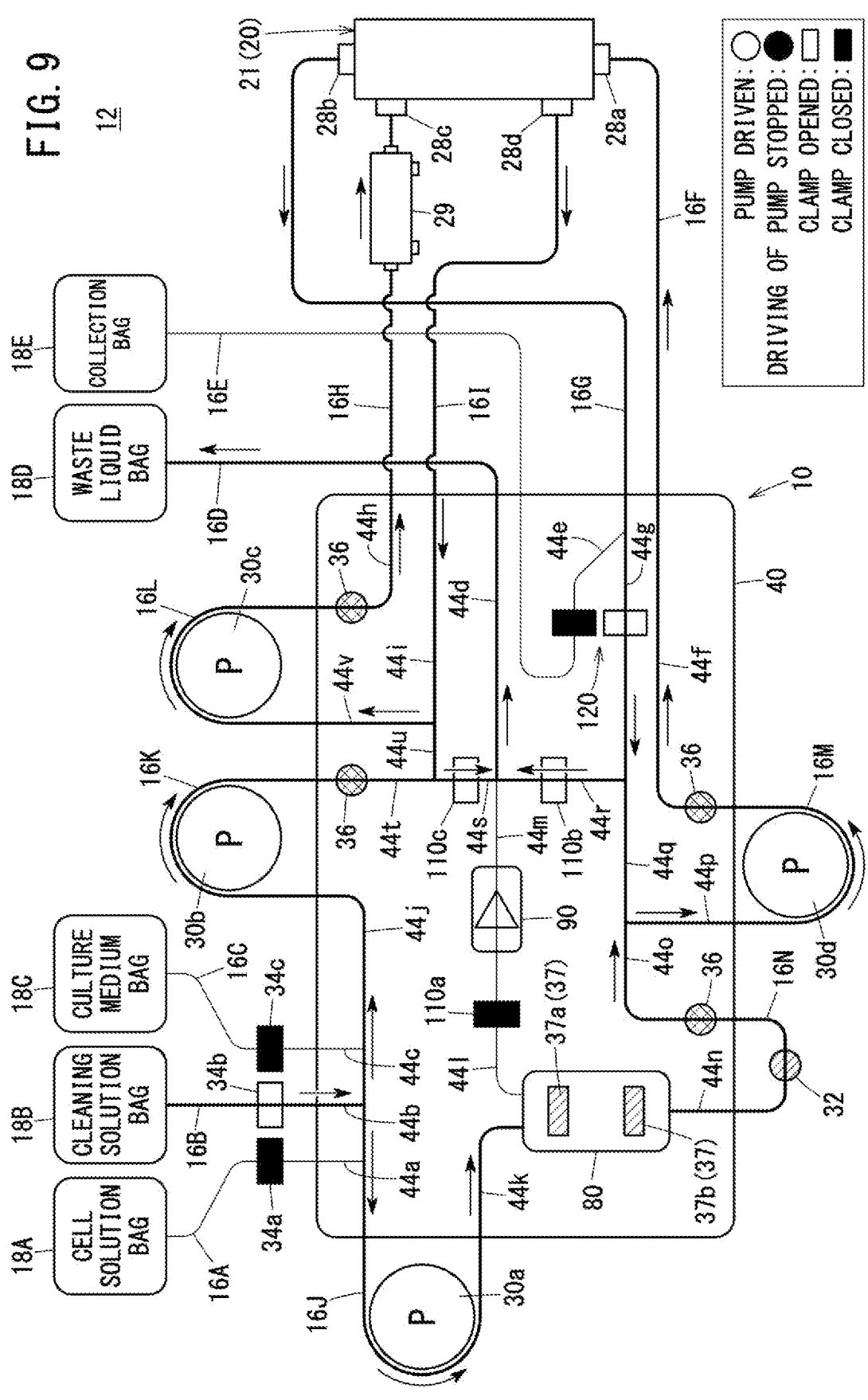
FIG. 9 is a first schematic diagram showing operations of the biological component treatment system according to embodiments of the present disclosure.

After having been set as described above, in the propagation process, a priming step as shown in FIG. 9 is executed. In the priming step, the cell propagation device 15 opens the second outer side clamp 34b, while on the other hand, closes the first and third outer side clamps 34a and 34c. Further, the cell propagation device 15 opens the second and third single clamp structures 110b and 110c, while on the other hand, closes the first single clamp structure 110a, and furthermore, in the switchable clamp structure 120, opens the second IC port path 44g, while on the other hand, closes the collection port path 44e.

Additionally, in the cell propagation device 15, the first to fourth pumps 30a to 30d are appropriately operated, and cause the cleaning solution in the cleaning solution bag 18B to flow into the bioreactor 21 and the waste liquid bag 18D. At this time, in the cell propagation system 23, the cleaning solution in the cleaning solution bag 18B passes through the two routes (the IC route and the EC route) inside the cassette 10, and the gas existing in the respective routes is removed.

In the IC route, the cleaning solution flows through the cleaning solution port path 44b, the first path 44j, the first pump tube 16J, the second path 44k, the liquid level target detection unit 80, the fifth path 44n, the sensor tube 16N, and the sixth path 44o, the seventh path 44p, the fourth pump tube 16M, and the first IC port path 44f, and is supplied to the first IC terminal 28*a* of the bioreactor 21 via the first IC tube 16F. In addition, the cleaning solution flows through the internal cavities of the hollow fibers 24 in the bioreactor 21 and to the side of the second IC terminal 28*b* while performing priming inside the hollow fibers 24, and the cleaning solution is returned to the second IC port path 44*g* of the cassette 10 via the second IC tube 16G. The cleaning solution that is returned to the cassette 10, under driving of the fourth pump 30*d*, passes through the eighth path 44*q* from the second IC port path 44*g*, flows again to the seventh path 44*p*, and circulates in the bioreactor 21 through the same pathway as described above. Further, under a state in which driving of the fourth pump 30*d* is stopped, the cleaning solution that is returned to the cassette 10 flows together with the gas through the ninth path 44*r* and the waste liquid port path 44*d*, and is discarded into the waste liquid bag 18D via the waste liquid tube 16D.

On the other hand, in the EC route, the cleaning solution flows through the cleaning solution port path 44*b*, the first path 44*j*, the second pump tube 16K, the eleventh path 44*t*, the twelfth path 44*u*, the thirteenth path 44*v*, the third pump tube 16L, and the first EC port path 44*h*, and is supplied to the first EC terminal 28*c* of the bioreactor 21 via the first EC tube 16H. When flowing through the first EC tube 16H, the cleaning solution passes through the gas exchanger 29, and is placed in a state in which an appropriate gas component is mixed therein. In addition, the cleaning solution flows to the side of the second EC terminal 28*d* through the outer side of the hollow fibers 24 (the main space 26*a*) in the bioreactor 21, and is returned to the second EC port path 44*i* of the cassette 10 via the second EC tube 16I. The cleaning solution that is returned to the cassette 10, under driving of the third pump 30*c*, flows once again to the thirteenth path 44*v* from the second EC port path 44*i*, and circulates in the bioreactor 21 through the same pathway as described above. Further, under a state in which driving of the third pump 30*c* is stopped, the cleaning solution that is returned to the cassette 10 flows together with the gas through the twelfth path 44*u*, the tenth path 44*s*, and the waste liquid port path 44*d*, and is discarded into the waste liquid bag 18D via the waste liquid tube 16D.

Figure 10:
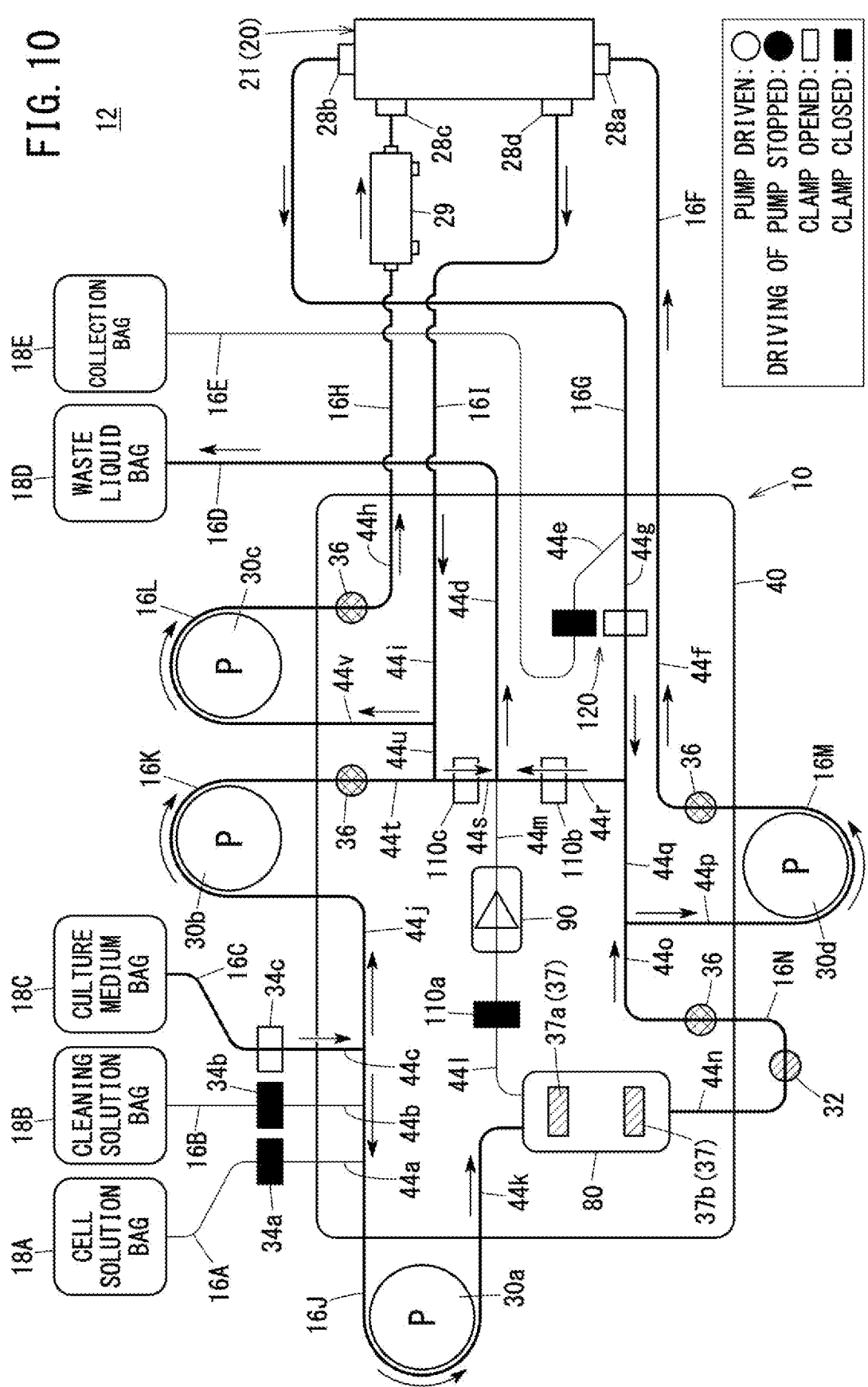
FIG. 10 is a second schematic diagram showing operations of the biological component treatment system according to embodiments of the present disclosure.

After completion of the aforementioned priming step, in the propagation process, a culture medium replacement step is performed as shown in FIG. 10. Consequently, the cell propagation system 23 fills the internal cavities of the hollow fibers 24 and the outer side (e.g., the main space 26*a*) of the bioreactor 21 with the culture medium. Moreover, in the cell propagation system 23, without executing the priming step, the culture medium replacement step may be executed first without executing the priming step, and the gas may be removed by the culture medium.

In the culture medium replacement step, the cell propagation device 15 opens the third outer side clamp 34*c*, while on the other hand, closes the first and second outer side clamps 34*a* and 34*b*. Further, the cell propagation device 15 opens the second and third single clamp structures 110*b* and 110*c*, while on the other hand, closes the first single clamp structure 110*a*, and furthermore, in the switchable clamp structure 120, opens the second IC port path 44*g*, while on the other hand, closes the collection port path 44*e*. Additionally, in the cell propagation device 15, the first to fourth pumps 30*a* to 30*d* are appropriately operated, and cause the culture medium in the culture medium bag 18C to flow into the bioreactor 21 and the waste liquid bag 18D.

The culture medium in the culture medium bag 18C is supplied to the bioreactor 21 by flowing through the IC route and the EC route, in the same manner as in the priming step.

More specifically, aside from also passing through the culture medium tube 16C and the culture medium port path 44*c*, the culture medium basically flows along the same route as in the priming step. Consequently, both the IC side and the EC side inside the bioreactor 21 can effect a replacement from the cleaning solution to the culture medium. Thus, a description of a route for the culture medium is omitted.

Figure 11:
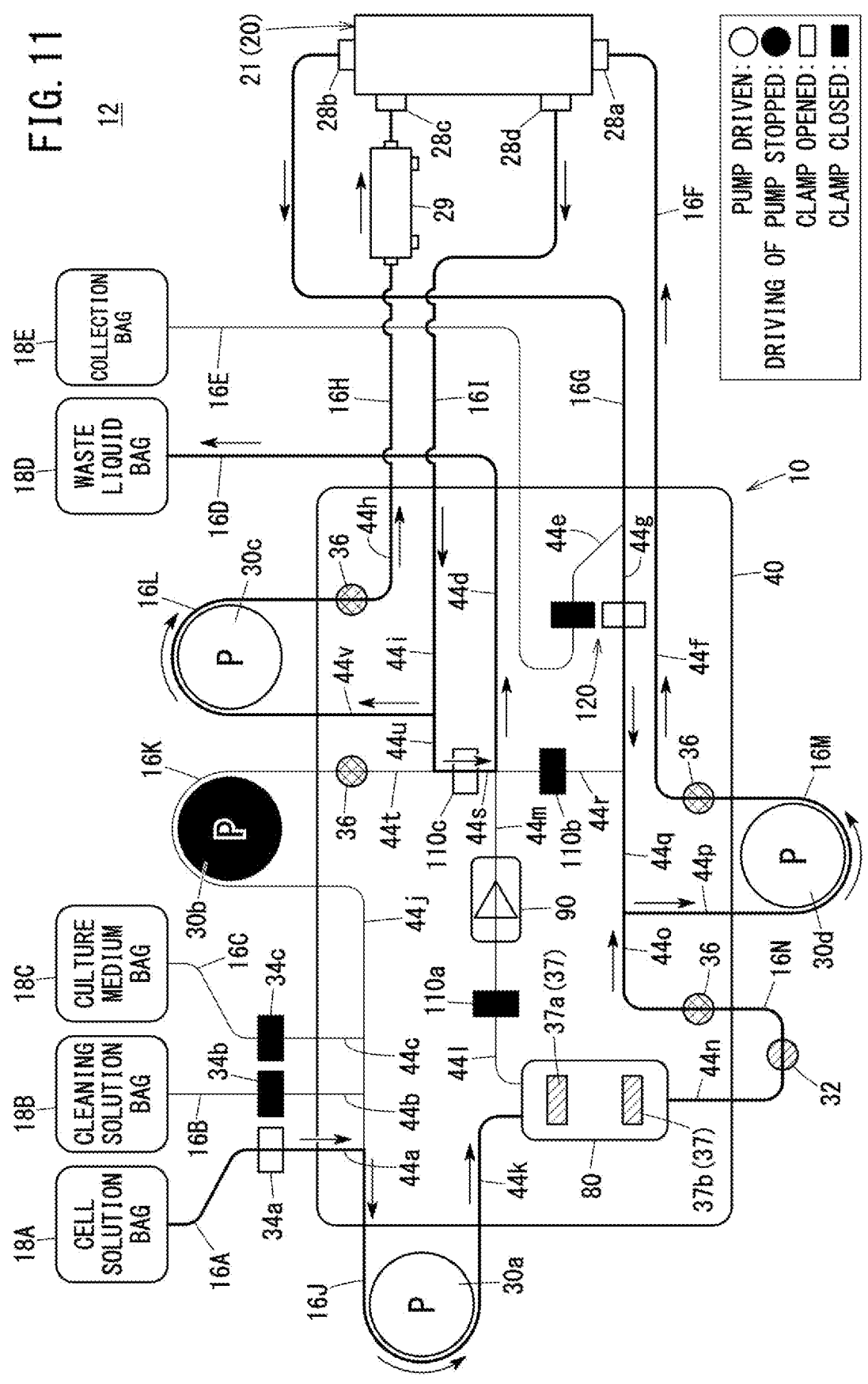
FIG. 11 is a third schematic diagram showing operations of the biological component treatment system according to embodiments of the present disclosure.

Following completion of the culture medium replacement step, in the propagation process, a cell seeding step is performed as shown in FIG. 11. In the seeding step, while the cell propagation system 23 supplies the cell solution to the bioreactor 21 via the IC route, the culture medium existing in the EC route is circulated, and the gas component is supplied to the bioreactor 21. In greater detail, the cell propagation device 15 opens the first outer side clamp 34*a*, while on the other hand, closes the second and third outer side clamps 34*b* and 34*c*. Further, the cell propagation device 15 opens the third single clamp structure 110*c*, while on the other hand, closes the first and second single clamp structures 110*a* and 110*b*, and furthermore, in the switchable clamp structure 120, opens the second IC port path 44*g*, while on the other hand, closes the collection port path 44*e*. Additionally, in the cell propagation device 15, the first, third, and fourth pumps 30*a*, 30*c*, and 30*d* are appropriately operated.

In the IC route, the cell solution, which has flowed from the cell solution bag 18A and through the cell solution tube 16A, flows in the cassette 10 through the cell solution port path 44*a*, the first path 44*j*, the first pump tube 16J, the second path 44*k*, the liquid level target detection unit 80, the fifth path 44*n*, the sensor tube 16N, the sixth path 44*o*, the seventh path 44*p*, the fourth pump tube 16M, and the first IC port path 44*f*. In addition, the cell solution is supplied from the cassette 10 to the first IC terminal 28*a* of the bioreactor 21 via the first IC tube 16F. When the cell solution flows to the side of the second IC terminal 28*b*, the cell solution is returned via the second IC tube 16G to the second IC port path 44*g* of the cassette 10. The cell solution that is returned to the cassette 10, under driving of the fourth pump 30*d*, passes through the eighth path 44*q* from the second IC port path 44*g*, flows again to the seventh path 44*p*, and circulates in the bioreactor 21 through the same pathway as described above. Further, a portion of the cell solution flows into the EC route (e.g., the main space 26*a*) through the pores of the hollow fibers 24 of the bioreactor 21, and flows out into the waste liquid bag 18D together with the culture medium in the EC route.

On the other hand, in the EC route, driving of the second pump 30*b* is stopped, and the third pump 30*c* is driven, whereby the culture medium supplied in the culture medium replacement step flows through the circulation circuit of the EC route. In this case, the culture medium flows through the thirteenth path 44*v*, the third pump tube 16L, and the first EC port path 44*h* inside the cassette 10, and is supplied to the first EC terminal 28*c* of the bioreactor 21 via the first EC tube 16H. When flowing through the first EC tube 16H, the culture medium passes through the gas exchanger 29, and is placed in a state in which an appropriate gas component is mixed therein, and in the bioreactor 21, the culture medium and the gas component are supplied to the cells from the main space 26*a* through the pores of the hollow fibers 24. Further, the culture medium in the main space 26*a* is returned to the cassette 10 from the side of the second EC terminal 28*d* and via the second EC tube 16I. Under driving of the third pump 30*c*, the culture medium that has been returned to the cassette 10 circulates in the bioreactor 21 through the same pathway as described above.

Figure 12:
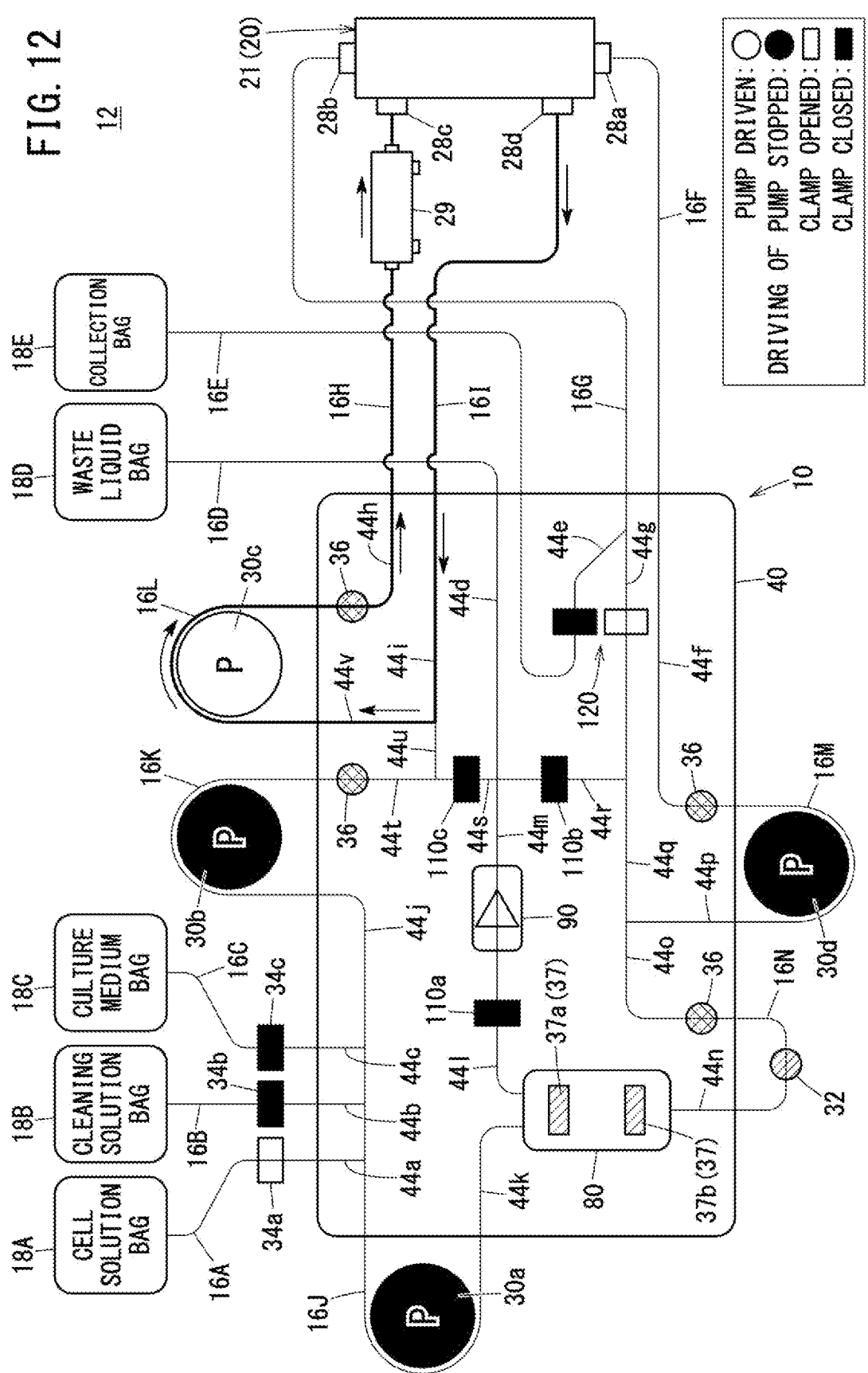
FIG. 12 is a fourth schematic diagram showing operations of the biological component treatment system according to embodiments of the present disclosure.

In addition, in the seeding step, when all of the cell solution in the cell solution bag 18A has been seeded, as shown in FIG. 12, operation of the first pump 30a and the fourth pump 30d is stopped (e.g., supplying and circulation of the cell solution are stopped), and the cells become adhered to the inner peripheral surfaces of the hollow fibers 24. At this time, in the cell propagation system 23, the tenth path 44s is closed by the third single clamp structure 110c, and while operation of the second pump 30b continues to be stopped, the third pump 30c is operated and the culture medium in the EC route is circulated. Consequently, supply of oxygen to the cells in the hollow fibers 24 is continued.

After completion of the seeding step, in the propagation process, returning to FIG. 10, a cell culturing step is executed. In the culturing step, the cell propagation system 23 supplies the culture medium from both the IC route and the EC route, and performs culturing of the cells that were seeded to the interior of the bioreactor 21. More specifically, in the culturing step, using the same routes as in the culture medium replacement step, supply and discharge of the culture medium is carried out, and the culturing step is carried out for a longer period of time (e.g., over several days) in comparison with the other steps, whereby the cells on the inner peripheral surfaces of the hollow fibers 24 are made to propagate. Therefore, in the cell propagation system 23, the culture medium is basically circulated in the IC route and the EC route, whereby the amount of the culture medium that is supplied can be suppressed, and costs can be reduced. Moreover, the cell propagation system 23 may be constituted to supply the culture medium to the bioreactor 21 using only one of either the IC route or the EC route. In accordance with this feature, it is possible to further promote a reduction in costs. For example, at a time of normal operation, only the first pump 30a may be operated, and the culture medium may be supplied to the bioreactor 21 from the IC route.

More specifically, the cell propagation device 15 opens the third outer side clamp 34c, while on the other hand, closes the first and second outer side clamps 34a and 34b. Further, the cell propagation device 15 opens the second and third single clamp structures 110b and 110c, while on the other hand, closes the first single clamp structure 110a, and furthermore, in the switchable clamp structure 120, opens the second IC port path 44g, while on the other hand, closes the collection port path 44e. Additionally, in the cell propagation device 15, the first to fourth pumps 30a to 30d are appropriately operated, and cause the culture medium in the culture medium bag 18C to flow into the bioreactor 21 and the waste liquid bag 18D.

At this time, the culture medium supplied to (and circulated through) the bioreactor 21 via the IC route moves from the internal cavities of the hollow fibers 24 to the outer side (e.g., the main space 26a) inside the bioreactor 21, whereby the culture medium then flows into the EC route. Since the second single clamp structure 110b is opened in the EC route, the culture medium which has been increased in the EC route can be appropriately discarded.

In addition, in the IC route, the liquid level of the culture medium is detected by the liquid level target detection unit 80, and the supplied amount of the culture medium supplied to the bioreactor 21 is adjusted. In this instance, at a time of normal operation, by the cell propagation device 15 closing the first single clamp structure 110a, the liquid level target detection unit 80 causes the culture medium to flow from the second path 44k to the fifth path 44n, and the culture medium is supplied appropriately to the circulation circuit of the IC route.

In addition, when air is excessively accumulated in the storage space 80a of the liquid level target detection unit 80 (e.g., the lower sensor 37b has detected the air), the first single clamp structure 110a is opened, and further, the supplied amount of the liquid is increased by the first pump 30a. Consequently, the amount of the culture medium that flows into the storage space 80a from the second path 44k becomes greater than the amount that flows out to the fifth path 44n from the storage space 80a, the liquid level of the culture medium is increased, and the air is released from the liquid level target detection unit 80. The air in the liquid level target detection unit 80 flows out from the cassette 10 through the third path 44l, the check valve unit 90, the fourth path 44m, and the waste liquid port path 44d, and is discharged to the waste liquid bag 18D via the waste liquid tube 16D. In addition, when the air sufficiently escapes from the liquid level target detection unit 80 (e.g., when the upper sensor 37a detects the liquid), the first single clamp structure 110a is closed again, and the supplied amount of the liquid is returned by the first pump 30a.

Figure 13:
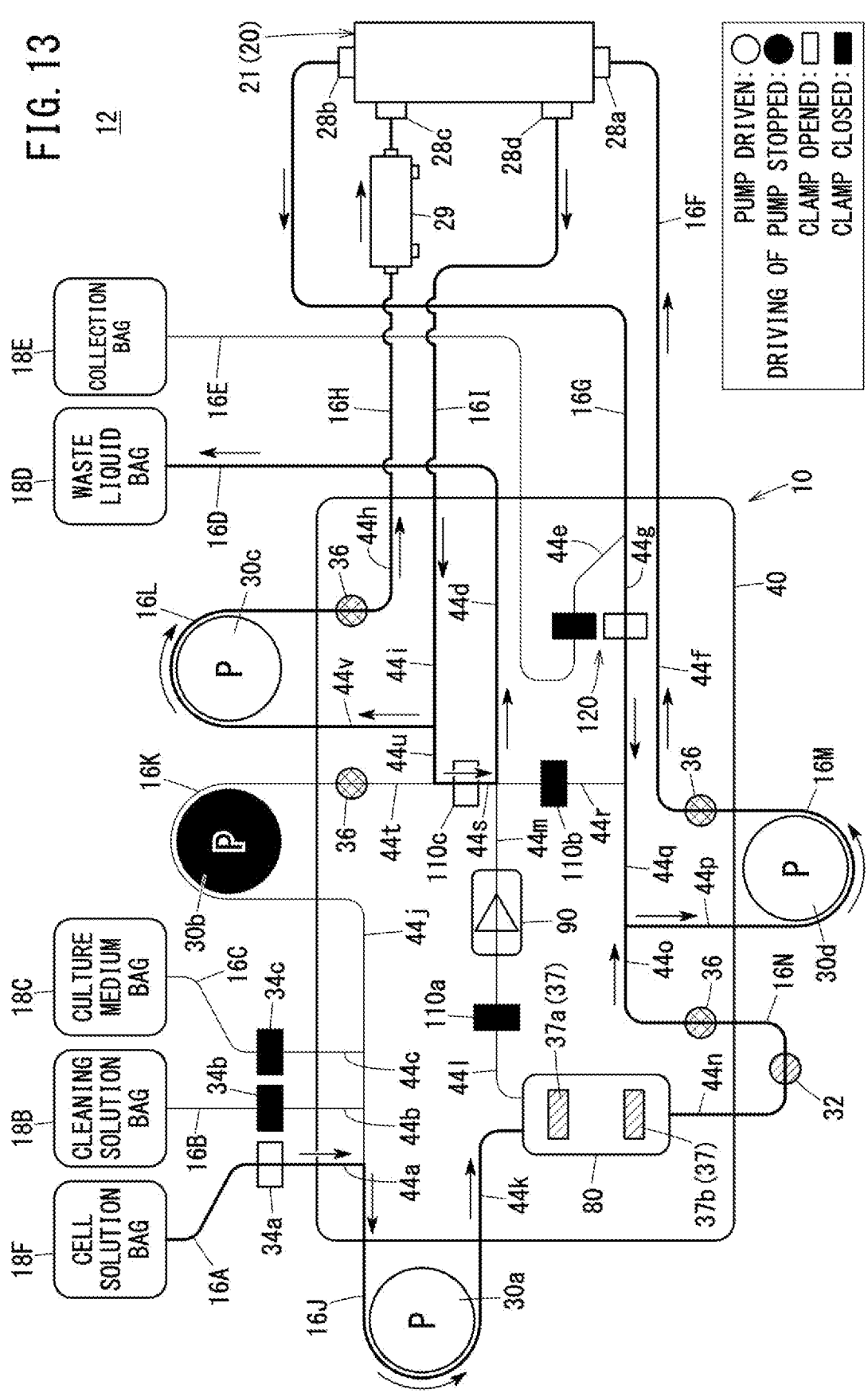
FIG. 13 is a fifth schematic diagram showing operations of the biological component treatment system according to embodiments of the present disclosure.

After completion of the culturing step, in the propagation process, a stripping step shown in FIG. 13 is executed. More specifically, in the cell propagation system 23, the stripping solution is supplied from the IC route to thereby strip off the cells that were cultured (e.g., propagated) inside the bioreactor 21. Further, in the stripping step, the culture medium containing the gas component is circulated in the EC route between the bioreactor 21.

In greater detail, the operator of the cell propagation system 23 performs an operation of removing the cell solution bag 18A from the cell solution tube 16A, and connecting the stripping solution bag 18F. Consequently, the kit 12 is placed in a state of being capable of supplying the stripping solution from the stripping solution bag 18F to the cassette 10 via the cell solution tube 16A. Therefore, the cell propagation device 15 opens the first outer side clamp 34a, while on the other hand, closes the second and third outer side clamps 34b and 34c. Further, the cell propagation device 15 opens the third single clamp structure 110c, while on the other hand, closes the first and second single clamp structures 110a and 110b, and furthermore, in the switchable clamp structure 120, opens the second IC port path 44g, while on the other hand, closes the collection port path 44e. Additionally, in the cell propagation device 15, the first, third, and fourth pumps 30a, 30c, and 30d are appropriately operated.

In the IC route, the stripping solution, which has flowed from the stripping solution bag 18F and through the cell solution tube 16A, flows in the cassette 10 through the cell solution port path 44a, the first path 44j, the first pump tube 16J, the second path 44k, the liquid level target detection unit 80, the fifth path 44n, the sensor tube 16N, the sixth path 44o, the seventh path 44p, the fourth pump tube 16M, and the first IC port path 44f. In addition, the stripping solution is supplied from the cassette 10 to the first IC terminal 28a of the bioreactor 21 via the first IC tube 16F. In the bioreactor 21, the stripping solution peels off the cells on the inner peripheral surfaces of the hollow fibers 24, when passing through the internal cavities of the hollow fibers 24. When the stripping solution flows to the side of the second IC terminal 28b, the stripping solution is returned via the second IC tube 16G to the second IC port path 44g of the cassette 10. The stripping solution that is returned to the cassette 10, under driving of the fourth pump 30d, passes through the eighth path 44*q* from the second IC port path 44*g*, flows again to the seventh path 44*p*, and circulates in the bioreactor 21 through the same pathway as described above. Further, a portion of the stripping solution flows into the EC route (e.g., the main space 26*a*) through the pores of the hollow fibers 24 of the bioreactor 21, and flows out into the waste liquid bag 18D together with the culture medium in the EC route.

On the other hand, in the EC route, driving of the second pump 30*b* is stopped, and the third pump 30*c* is driven, whereby the culture medium supplied in the culturing step is circulated through the circulation circuit of the EC route. Consequently, the culture medium and the gas component are supplied to the cells inside the hollow fibers 24 even during the stripping step.

Figure 14:
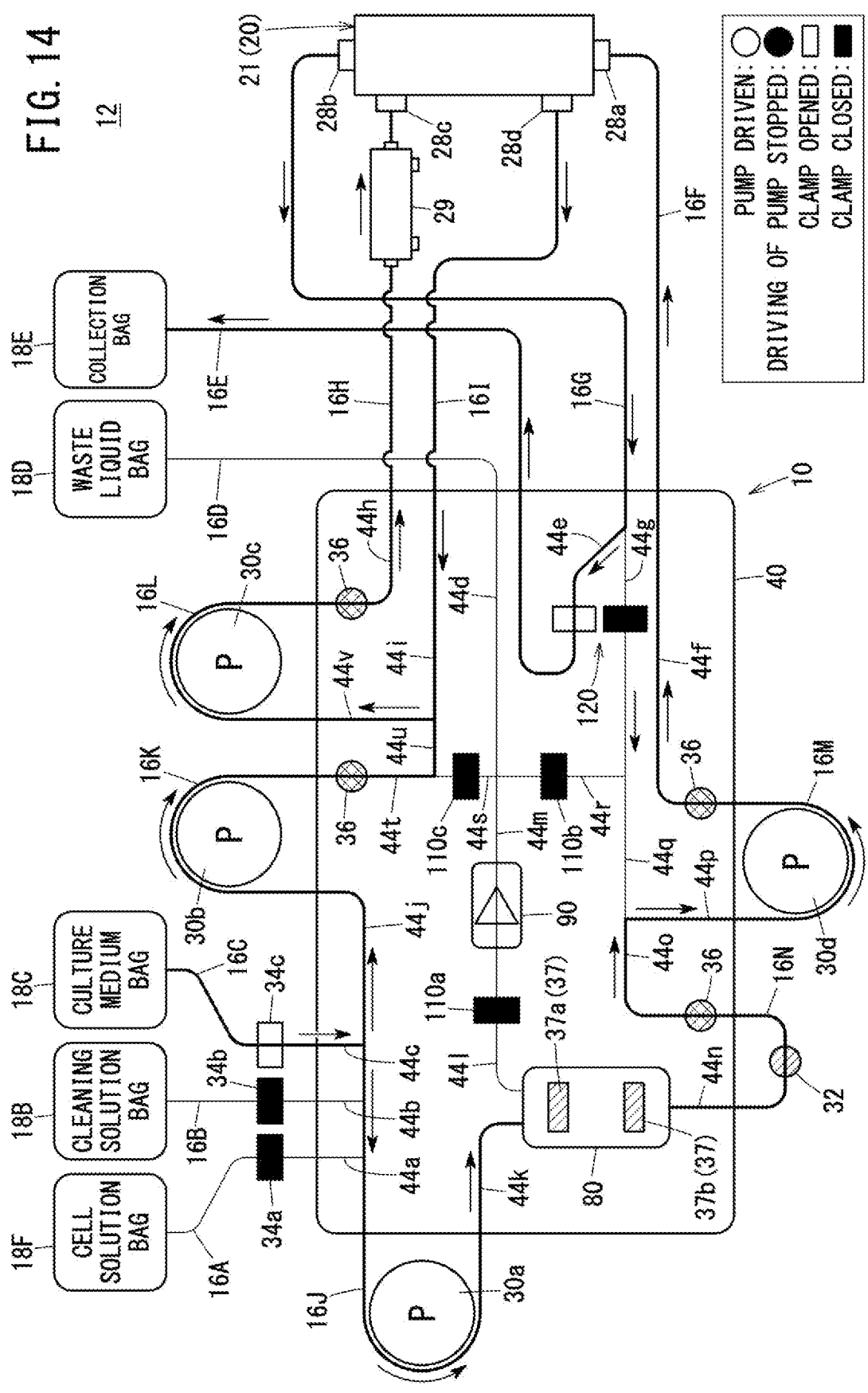
FIG. 14 is a sixth schematic diagram showing operations of the biological component treatment system according to embodiments of the present disclosure.

After completion of the stripping step, in the propagation process, a collecting step shown in FIG. 14 is executed. In the collecting step, in the cell propagation system 23, by supplying the culture medium to the IC route, the cells that were stripped off in the stripping step are made to flow out from the bioreactor 21 and are guided into the collection bag 18E. At this time, the culture medium and the gas component are also supplied through the EC route.

More specifically, the cell propagation device 15 opens the third outer side clamp 34*c*, while on the other hand, closes the first and second outer side clamps 34*a* and 34*b*. Further, the cell propagation device 15 closes the first to third single clamp structures 110*a*, 110*b*, and 110*c*, and furthermore, in the switchable clamp structure 120, opens the collection port path 44*e* and closes the second IC port path 44*g*. Additionally, in the cell propagation device 15, the first to fourth pumps 30*a* to 30*d* are appropriately operated, and cause the culture medium in the culture medium bag 18C to flow into the bioreactor 21, and further, guide cells in the bioreactor 21 to the collection bag 18E.

More specifically, in the IC route, the culture medium, which has flowed from the culture medium bag 18C and through the culture medium tube 16C, flows in the cassette 10 through the culture medium port path 44*c*, the first path 44*j*, the first pump tube 16J, the second path 44*k*, the liquid level target detection unit 80, the fifth path 44*n*, the sensor tube 16N, the sixth path 44*o*, the seventh path 44*p*, the fourth pump tube 16M, and the first IC port path 44*f*. Then, the culture medium is supplied from the cassette 10 to the first IC terminal 28*a* of the bioreactor 21 via the first IC tube 16F, and the cells in the cavities of the hollow fibers 24 are washed away. When the cells and the culture medium (hereinafter referred to as a culture) flows to the side of the second IC terminal 28*b*, the culture is returned via the second IC tube 16G to the second IC port path 44*g* of the cassette 10. Inside the cassette 10, by the second IC port path 44*g* being closed by the switchable clamp structure 120, the culture flows from an intermediate position of the second IC port path 44*g* to the collection port path 44*e*. In addition, the culture is discharged to the exterior of the cassette 10 from the collection port path 44*e*, and flows into the collection bag 18E via the collection tube 16E.

On the other hand, in the EC route, the culture medium flows through the culture medium port path 44*c*, the first path 44*j*, the second pump tube 16K, the eleventh path 44*t*, the twelfth path 44*u*, the thirteenth path 44*v*, the third pump tube 16L, and the first EC port path 44*h*. In addition, the culture medium enters into a state in which the gas component is mixed by passing through the first EC tube 16H, and while supplying the gas component to the cells in the bioreactor 21, the culture medium is returned to the second EC port path 44*i* of the cassette 10 from the main space 26*a* via the second EC tube 16I. The culture medium returned to the cassette 10, under driving of the third pump 30*c*, flows once again to the thirteenth path 44*v* from the second EC port path 44*i*, and circulates in the bioreactor 21 through the same pathway as described above.

By the aforementioned steps, in the cell propagation system 23, the cells that were cultured in the bioreactor 21 can be satisfactorily stored in the collection bag 18E. Moreover, the control on the basis of detecting the liquid level by the liquid level target detection unit 80 (opening and closing of the first single clamp structure 110*a*) is not limited to being performed in the culturing step, and can naturally be performed in other steps. Further, the present disclosure is not limited to embodiments discussed thus far, and various modifications can be adopted in accordance with the essence and gist of the present disclosure.

Figure 15:
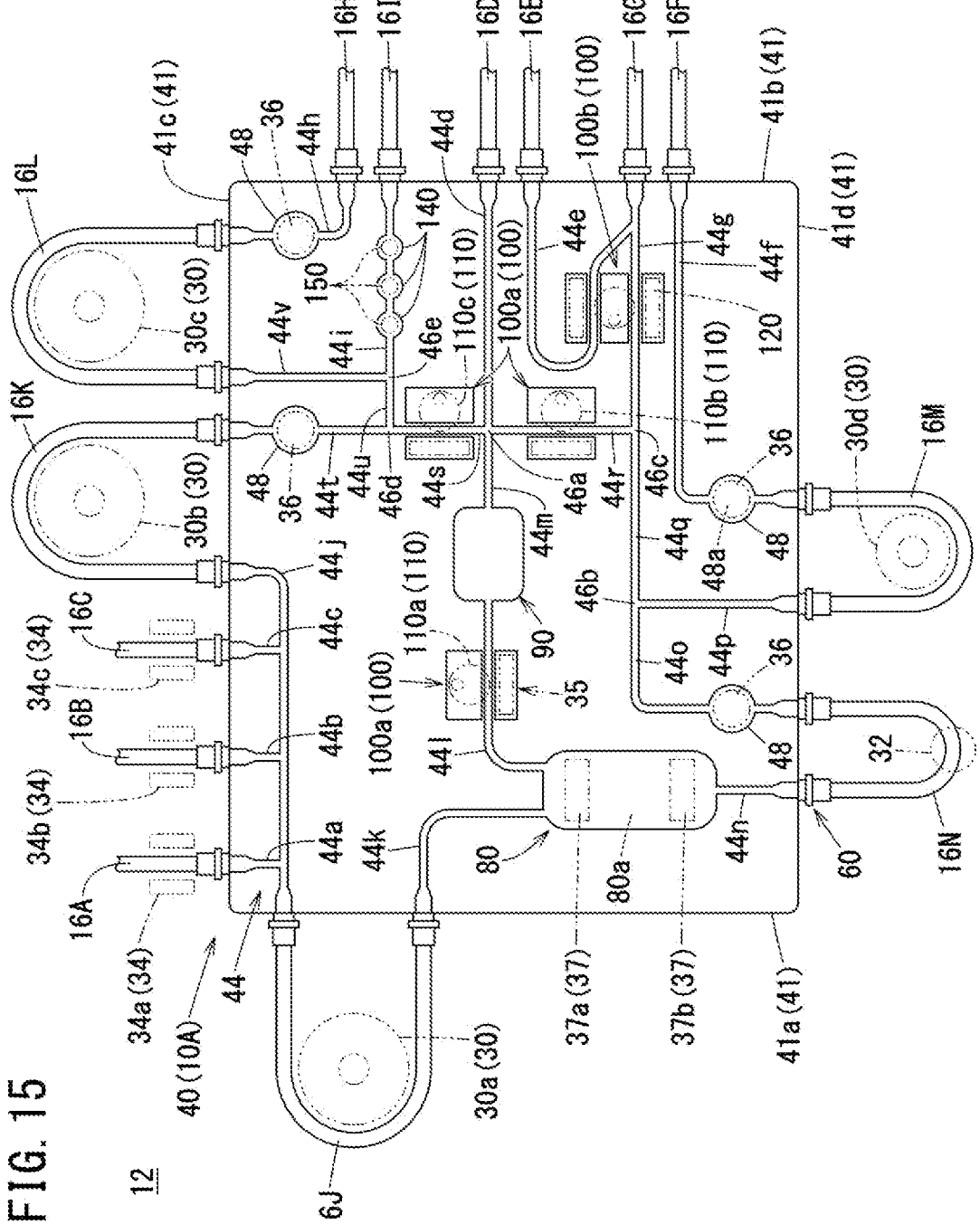
FIG. 15 is a plan view showing a biological component cassette and a peripheral portion thereof according to embodiments of the present disclosure.

For example, as shown in FIG. 15, a cassette 10A according to another embodiment may have constitution in which one or more (e.g., three as shown in FIG. 15) target detection units 140 which are capable of detecting a state of the liquid flowing through the flow paths 44. Each of the target detection units 140 comprises, for example, a fluorescent chip (not shown) that causes any one (or all) of dissolved oxygen, dissolved carbon dioxide, a pH, glucose, lactic acid, etc., contained within the liquid, to be detected, and the fluorescent chip is fixed to one of the inner surfaces from among the pair of resin sheets 42. In the set state, optical sensors 150 of the cell propagation device 15 are arranged in facing relation to the target detection units 140. As an example, the target detection units 140 are provided in the second EC port path 44*i*, and are constituted so as to have a larger cross-sectional area than the second EC port path 44*i*. Moreover, the target detection units 140 may be provided in the second IC port path 44*g* or the like.

Figure 8A:
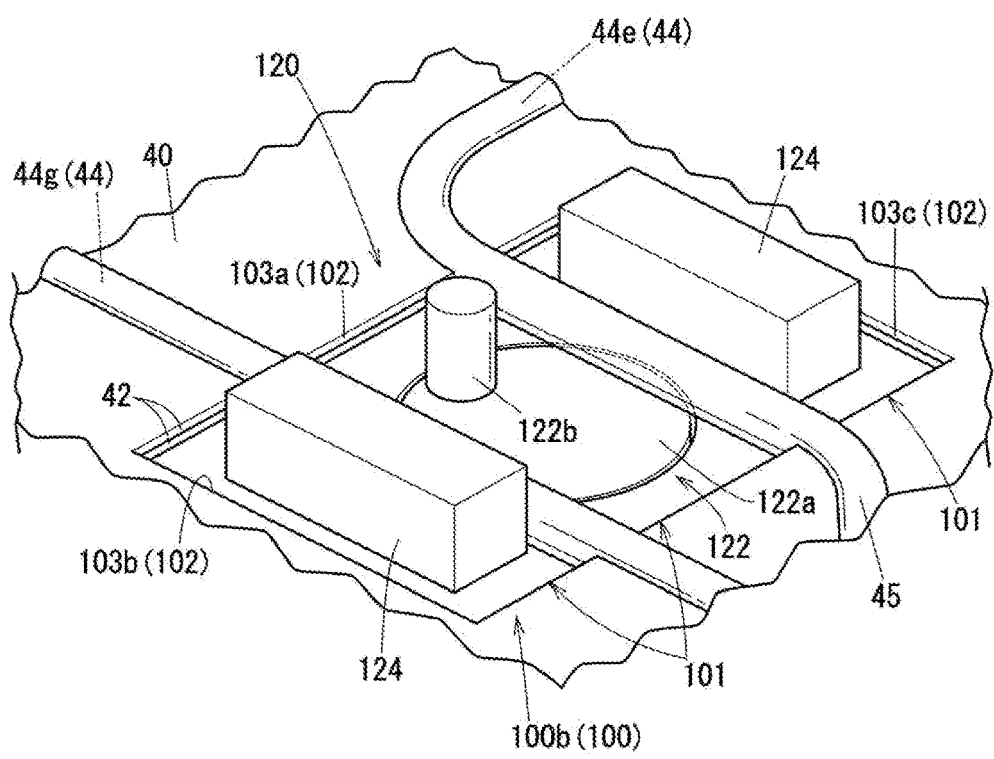
FIG. 8A is an enlarged perspective view showing a multiple flow path opening/closing unit and an opened state of flow paths of a switchable clamp structure according to embodiments of the present disclosure.
Figure 8B:
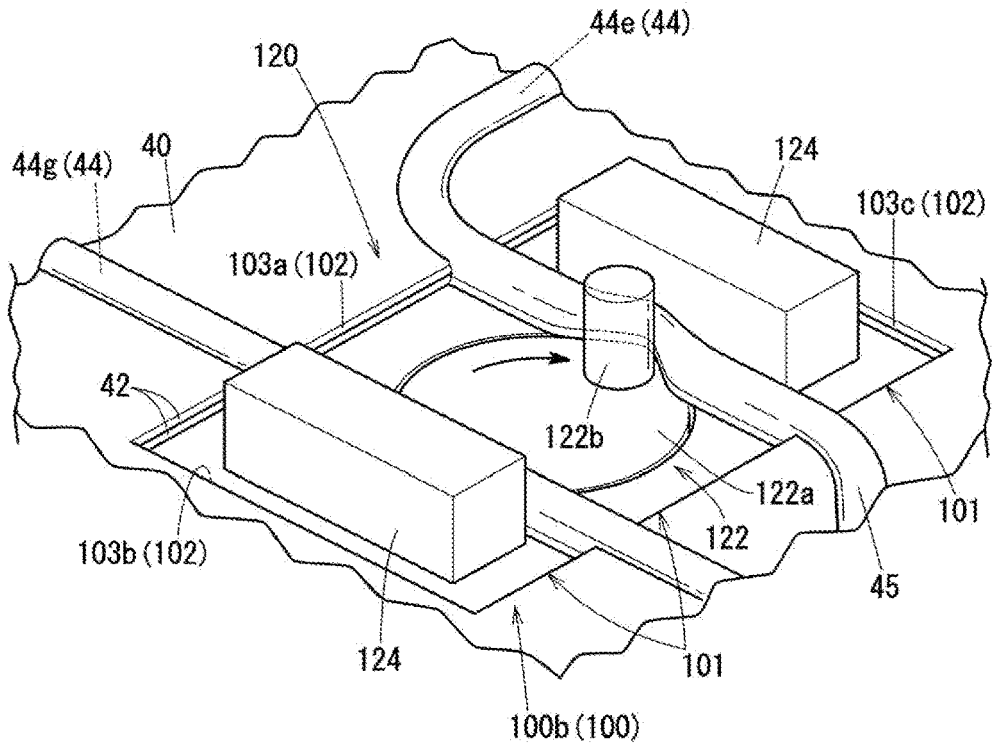
FIG. 8B is an enlarged perspective view showing the multiple flow path opening/closing unit and a closed state of one of the flow paths of the switchable clamp structure according to embodiments of the present disclosure.
Figure 16A:
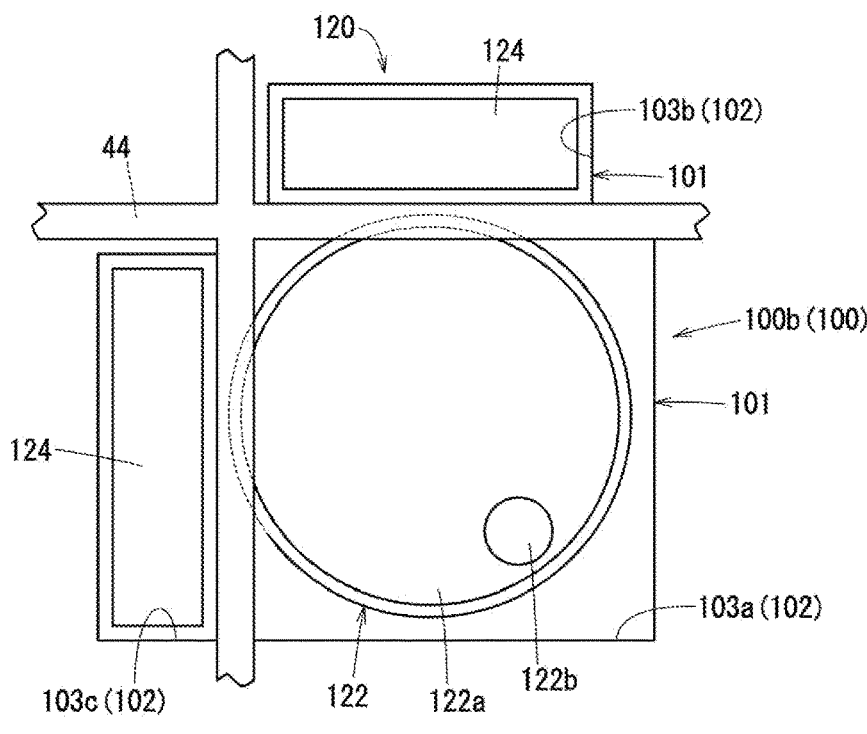
FIG. 16A is a plan view showing a multiple flow path opening/closing unit and a switchable clamp structure according to a first modification according to embodiments of the present disclosure.
Figure 16B:
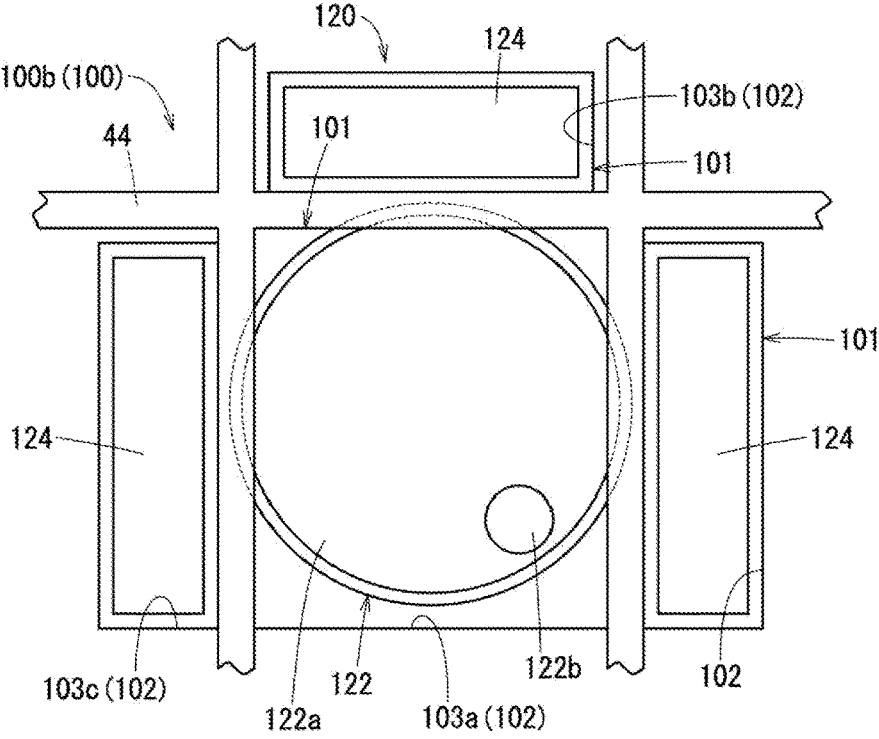
FIG. 16B is a plan view showing a multiple flow path opening/closing unit and a switchable clamp structure according to a second modification according to embodiments of the present disclosure.

Further, as described above, the multiple flow path opening/closing unit 100*b* and the switchable clamp structure 120 are configured to close a pair of flow paths 44 that extend mutually in parallel to each other (see, e.g., FIGS. 8A and 8B). However, the present disclosure is not limited to such configurations, and the multiple flow path opening/closing unit 100*b* and the switchable clamp structure 120 may be configured to close perpendicular flow paths 44 as shown in FIG. 16A, and as shown in FIG. 16B, three or more of the flow paths 44 may be opened or closed.

The single clamp structure 110 and the switchable clamp structure 120 are not limited to the rotation of pins 112*b* and 122*b* (displacement bodies), and the pins 112*b* and 122*b* may be or comprise, for example, a displacement body capable of moving reciprocally in a linear direction.

Furthermore, the flow path opening/closing unit 100 may include one single cutout 102 arranged at a position adjacent to a side of the flow paths 44. More specifically, if a fixed body (not shown) projects out at a joined location of the resin sheets 42 where the cutouts 102 are not disposed, by deforming the resin sheets 42 which possess flexibility, the fixed body can be arranged at a position in close proximity to the side of the flow paths 44. Thus, by displacing the pin 112*b* arranged in the cutouts 102, and sandwiching the flow path 44 between the pin 112*b* and the fixed body, the flow path 44 is capable of being closed.

At least some of the technical concepts, benefits, and effects will be described below.

The first aspect of the present disclosure includes the biological component cassette 10 or 10A having the flow path 44 in the interior thereof through which the liquid containing at least one biological component is allowed to flow, and including the cassette main body 40 formed in a sheet shape that possesses flexibility, wherein the cassette main body 40 includes the flow path opening/closing unit 100 configured to switch between opening and closing of the flow path 44, and the flow path opening/closing unit 100 includes the cutout 102 provided at the position adjacent to the flow path 44, and which is cut out of the cassette main body 40 in the thickness direction.

Ease of usage of the biological component cassette 10 or 10A can be further enhanced by providing the flow path opening/closing unit 100 in the cassette main body 40 that possesses flexibility and is equipped with the flow path 44 through which the liquid flows. More specifically, when the biological component cassette 10 or 10A is set by an operator in the biological component treatment device 14, the plurality of pathways can be arranged easily and accurately. At this time, the cutout 102 of the flow path opening/closing unit 100 is also easily arranged in the inner side clamp 35 of the device accompanying the arrangement of the cassette main body 40, and at the time of processing, the flow path 44 can be easily opened and closed. Consequently, the time and effort of the operator can be significantly reduced.

Further, the flow path opening/closing unit 100 includes the pair of cutouts 102 on both sides sandwiching the flow path 44 therebetween. In accordance with this feature, when set, the biological component cassette 10 or 10A is arranged in the biological component treatment device 14 in a manner so that the flow path 44 can be easily sandwiched between the pair of cutouts 102. Accordingly, it becomes possible for the flow path 44 to be opened and closed more reliably.

Further, the cutouts 102 are formed in rectangular shapes elongated in a direction in which the flow path 44 extends and at the positions adjacent to the flow path 44. In accordance with this feature, while the flow path 44 extends in a linear shape, the flow path opening/closing unit 100 is capable of causing the inner side clamp 35 of the biological component treatment device 14 to be more smoothly inserted into the cutouts 102.

Further, from among the pair of cutouts 102, a length in a lateral direction of one of the cutouts 102 is longer than a length in the lateral direction of another one of the cutouts 102. In accordance with this feature, in the flow path opening/closing unit 100, while the displaceable body (the pin 112b or 122b) of the inner side clamp 35 is easily disposed in one of the cutouts 102, the fixed body (114 or 124) can be easily disposed in the other one of the cutouts 102.

The flow path opening/closing unit 100 (the multiple flow path opening/closing unit 100b) includes the cutouts 102 lying adjacent to the plurality of flow paths 44. In accordance with this feature, the flow path opening/closing unit 100 is capable of selectively opening or closing the plurality of flow paths 44 by the displaceable body (the pin 122b), which is arranged in the cutout 102 (the first cutout 103a) lying adjacent to the plurality of flow paths 44.

Further, the plurality of flow paths 44 include a first flow path (the second IC port path 44g) and a second flow path (the collection port path 44e) extending in parallel to each other, and the flow path opening/closing unit 100 (the multiple flow path opening closing unit 100b) includes the first cutout 103a sandwiched between the first flow path and the second flow path, the second cutout 103b provided on a side opposite from the first cutout 103a while sandwiching the first flow path therebetween, and the third cutout 103c provided on a side opposite from the first cutout 103a while sandwiching the second flow path therebetween. In accordance with such features, concerning the first flow path and the second flow path that extend in parallel to each other, while one of the flow paths is open, the flow path opening/closing unit 100 is capable of closing the other one of the flow paths. Further, by adopting the multiple flow path opening/closing unit 100b, it is possible to suppress the number of installed inner side clamps 35 and to reduce costs.

Further, the cassette main body 40 is formed by joining together the pair of resin sheets 42, and so as to include the flow path 44 between the resin sheets 42, and the flow path opening/closing unit 100 includes the flow path wall 45 made up from the pair of resin sheets 42 that constitute the flow path 44, and the joined location where the pair of resin sheets 42 are joined together within a range from the flow path wall 45 to the cutout 102, and the flow path 44 is closed by collectively deforming the flow path wall 45 and the joined location, based on displacement of the displaceable body (the pin 112b or 122b) which is inserted into the cutout 102. In accordance with such features, the flow path opening/closing unit 100 is capable of opening and closing the flow path 44 in a more satisfactory manner.

Further, the second aspect of the present disclosure is characterized by the biological component cassette 10 or 10A having the flow path 44 in the interior thereof through which the liquid containing at least one biological component is allowed to flow, and including the cassette main body 40 formed in a sheet shape that possesses flexibility, wherein the cassette main body 40 is constituted by joining together the pair of resin sheets 42, and so as to include the flow path 44 between the resin sheets 42, and at least a portion of the flow path 44 in the cassette main body 40 includes the sheet separating portion 101 in which the outer circumferential surface of the flow path 44 is separated from the resin sheets 42 over the entire circumference thereof. In accordance with such features, in the biological component cassette 10 or 10A, the plurality of pathways can be easily and accurately arranged, and the flow paths 44 can be easily opened and closed.

Further, the flow path 44 constitutes the flow path opening/closing unit 100 configured to switch between opening and closing of the flow path 44 in the sheet separating portion 101. In accordance with this feature, the biological component cassette 10 or 10A can suitably carry out opening and closing of the flow path 44 through the sheet separating portion 101.

The sheet separating portions 101 are constituted by the cutout 102 which is cut out of the cassette main body 40. In accordance with this feature, with a simple technique, the biological component cassette 10 or 10A can be formed in a state in which the outer circumferential surface of the flow path 44 is separated from the resin sheet 42 over the entire circumference thereof.

Further, the third aspect of the present disclosure is characterized by the biological component kit 12, including the tube 16 through which the liquid containing at least one biological component is allowed to flow, and the biological component cassette 10 or 10A to which the tube 16 is connected, wherein the biological component cassette 10 or 10A has the flow path 44 in the interior thereof through which the liquid is allowed to flow, and including the cassette main body 40 formed in a sheet shape that possesses flexibility, the cassette main body 40 includes the flow path opening/closing unit 100 configured to switch between opening and closing of the flow path 44, and the flow path opening/closing unit 100 includes the cutout 102 provided at the position adjacent to the flow path 44, and which is cut out of the cassette main body 40 in the thickness direction. In accordance with such features, when set by an operator in the biological component treatment device 14, the biological component kit 12 allows the plurality of pathways to be easily and accurately arranged, and further, the flow path opening/closing unit 100 is easily arranged in the inner side clamp 35 of the device. Accordingly, the biological component kit 12 can further enhance ease of usage.

Further, the fourth aspect of the present disclosure is characterized by the biological component treatment system 22, including the biological component kit 12 including the tube 16 through which the liquid containing at least one biological component is allowed to flow, and the biological component cassette 10 to which the tube 16 is connected, and the biological component treatment device 14 in which the biological component kit 12 is set, wherein the biological component cassette 10 has the flow path 44 in the interior thereof through which the liquid is allowed to flow, and includes the cassette main body 40 formed in a sheet shape that possesses flexibility, the cassette main body 40 includes the flow path opening/closing unit 100 configured to switch between opening and closing of the flow path 44, the flow path opening/closing unit 100 includes the cutout 102 provided at the position adjacent to the flow path 44, and which is cut out of the cassette main body 40 in the thickness direction, and the biological component treatment device 14 includes the displaceable body (the pin 112*b* or 122*b*) inserted into the cutout 102 in a set state of the biological component kit 12, and which is configured to open and close the flow path 44 in accordance with a displacement operation. In accordance with such features, in the biological component treatment system 22, the biological component cassette 10 or 10A having the flow path opening/closing unit 100, and the biological component kit 12 can be easily set in the biological component treatment device 14, and ease of usage can be further enhanced.

Further, the biological component treatment device 14 includes the rotating member (the rotating bodies 112 and 122) that rotates the displaceable body (the pin 112*b* or 122*b*) along a planar direction of the cassette main body 40. In accordance with this feature, by rotating the rotating member, the biological component treatment device 14 can easily carry out opening and closing of the flow path 44. Moreover, the configuration for closing the flow path 44 of the cassette main body 40 need not necessarily be limited to rotating the displaceable body by the rotating member, and for example, chuck-type mechanisms or the like may be adopted in which the displaceable body moves reciprocally in a linear form to crush the flow path 44.

Further, the flow path opening/closing unit 100 includes the pair of cutouts 102 on both sides sandwiching the flow path 44 therebetween, and the biological component treatment device 14 inserts the displaceable body (the pin 112*b* or 122*b*) into one of the pair of cutouts 102, while inserts the non-displaceable fixed body 114 or 124 into another one of the pair of cutouts 102, and closes the flow path 44 based on a proximity of the displaceable body with respect to the fixed body 114 or 124. In accordance with such features, the biological component treatment system 22 is capable of easily and reliably closing the flow path 44 by sandwiching the flow path 44 between the fixed body 114 or 124 and the displaceable body that is inserted into the pair of cutouts 102.

What is claimed is:

1. A biological component cassette, comprising:
   a cassette main body formed in a sheet shape that possesses flexibility;

a first flow path in an interior of the cassette main body through which a liquid containing at least one biological component is allowed to flow;
   a second flow path in the interior of the cassette main body through which the liquid containing at least one biological component is allowed to flow; and
   a flow path opening/closing portion that accommodates structures configured to selectively open and close the first and second flow paths, wherein the flow path opening/closing portion includes:
      a first cutout disposed in the cassette main body in a thickness direction and at a first position adjacent to a first side of the first flow path;
      a second cutout disposed in the cassette main body in the thickness direction and at a second position adjacent to a first side of the second flow path; and
      a third cutout disposed in the cassette main body in the thickness direction and at a third position adjacent to respective second sides of the first and second flow paths such that the first flow path passes between the first cutout and the third cutout and the second flow path passes between the second cutout and the third cutout.

2. The biological component cassette of claim 1, wherein a length in a lateral direction of the third cutout is longer than lengths in the lateral direction of the first cutout and the second cutout.

3. The biological component cassette of claim 1, wherein the first cutout, the second cutout, and the third cutout are formed in rectangular shapes elongated in a direction in which the first flow path extends.

4. The biological component cassette of claim 3, wherein a length in a lateral direction of the third cutout is longer than a length in the lateral direction of the first cutout.

5. The biological component cassette of claim 1, wherein a length in a lateral direction of the third cutout is longer than a length in the lateral direction of the first cutout.

6. The biological component cassette of claim 1, wherein the first flow path and the second flow path are parallel to each other over a length of the first, second, and third cutouts.

7. The biological component cassette of claim 1,
   wherein the cassette main body is formed by joining together a pair of resin sheets, with the first and second flow paths disposed between the resin sheets, and
   wherein the third cutout is sized to accommodate a displaceable body that is controlled to selectively open and close the first and second flow paths.

8. A biological component cassette, comprising:
   a cassette main body formed in a sheet shape that possesses flexibility, the cassette main body formed by joining together a pair of resin sheets with a plurality of flow paths between the resin sheets;
   a first flow path in an interior of the cassette main body through which a liquid containing at least one biological component is allowed to flow;
   a second flow path in the interior of the cassette main body through which the liquid containing at least one biological component is allowed to flow; and
   a sheet separating portion in which entire outer circumferential surfaces of the first and second flow paths are separated from the resin sheets, the sheet separating portion including:
      a first cutout disposed in the cassette main body at a first position adjacent to a first side of the first flow path;

a second cutout disposed in the cassette main body at a second position adjacent to a first side of the second flow path; and a third cutout disposed in the cassette main body at a third position adjacent to respective second sides of the first and second flow paths such that the first flow path passes between the first cutout and the third cutout and the second flow path passes between the second cutout and the third cutout.

9. The biological component cassette of claim 8, wherein the first, second, and third cutouts are sized to accommodate structures configured to selectively open and close the first and second flow paths in the sheet separating portion.

10. The biological component cassette of claim 8, wherein a length in a lateral direction of the third cutout is longer than lengths in the lateral direction of the first cutout and the second cutout.

11. A biological component kit, comprising:

a tube through which a liquid containing at least one biological component is allowed to flow; and a biological component cassette to which the tube is connected, wherein the biological component cassette comprises:

a cassette main body formed in a sheet shape that possesses flexibility;

a first flow path in an interior of the cassette main body through which the liquid containing at least one biological component is allowed to flow;

a second flow path in the interior of the cassette main body through which the liquid containing at least one biological component is allowed to flow; and a flow path opening/closing portion that accommodates structures configured to selectively open and close the first and second flow paths, wherein the flow path opening/closing portion includes:

a first cutout disposed in the cassette main body in a thickness direction and at a first position adjacent to a first side of the first flow path;

a second cutout disposed in the cassette main body in the thickness direction and at a second position adjacent to a first side of the second flow path; and a third cutout disposed in the cassette main body in the thickness direction and at a third position adjacent to respective second sides of the first and second flow paths such that the first flow path passes between the first cutout and the third cutout and the second flow path passes between the second cutout and the third cutout.

12. The biological component kit of claim 11, wherein a length in a lateral direction of the third cutout is longer than lengths in the lateral direction of the first cutout and the second cutout.

13. The biological component kit of claim 11, wherein the first cutout, the second cutout, and the third cutout are rectangularly-shaped and extend along a first direction.

14. The biological component kit of claim 13, wherein a length in a lateral direction of the third cutout is longer than a length in the lateral direction of the second cutout.

15. The biological component kit of claim 11, wherein the first flow path and the second flow path are parallel to each other over a length of the first, second, and third cutouts.

16. The biological component kit of claim 11, wherein a length in a lateral direction of the third cutout is longer than a length in the lateral direction of the first cutout.

17. The biological component kit of claim 15, further comprising:

a displaceable body insertable into the third cutout, the displaceable body configured to open and close the flow path when displaced.

18. A biological component treatment system, comprising:

a biological component kit including a tube through which a liquid containing at least one biological component is allowed to flow, and a biological component cassette to which the tube is connected; and a biological component treatment device in which the biological component kit is set, wherein the biological component cassette comprises:

a cassette main body formed in a sheet shape that possesses flexibility;

a first flow path in an interior of the cassette main body through which the liquid containing at least one biological component is allowed to flow;

a second flow path in the interior of the cassette main body through which the liquid containing at least one biological component is allowed to flow; and a flow path opening/closing portion that accommodates structures configured to selectively open and close the first and second flow paths, wherein the flow path opening/closing portion includes:

a first cutout disposed in the cassette main body in a thickness direction and at a first position adjacent to a first side of the first flow path;

a second cutout disposed in the cassette main body in the thickness direction and at a second position adjacent to a first side of the second flow path; and a third cutout disposed in the cassette main body in the thickness direction and at a third position adjacent to respective second sides of the first and second flow paths such that the first flow path passes between the first cutout and the third cutout and the second flow path passes between the second cutout and the third cutout, and wherein the biological component treatment device includes a displaceable body inserted into the third cutout in a set state of the biological component kit, and which is configured to open and close the first and second flow paths when displaced.

19. The biological component treatment system of claim 18, wherein the displaceable body comprises a rotating member and a pin extending from the rotating member.

20. The biological component treatment system of claim 18, wherein the biological component treatment device comprises a first non-displaceable fixed body insertable into the first cutout.

\* \* \* \* \*